(12) United States Patent
Yohda et al.

(10) Patent No.: US 8,633,008 B2
(45) Date of Patent: Jan. 21, 2014

(54) BACTERIUM THAT CAN PERFORM COMPLETE DECHLORINATION OF TRICHLOROETHENE AND THE METHOD TO DECHLORINATE SOILS OR GROUND WATER CONTAMINATED WITH TRICHLOROETHENE USING THE BACTERIUM

(75) Inventors: Masafumi Yohda, Tokyo (JP); Mizuki Kitajima, Tokyo (JP); Noriyoshi Tamura, Tokyo (JP); Megumi Iwamoto, Tokyo (JP); Tomomi Fukuda, Tokyo (JP)

(73) Assignees: PaGE Science Co., Ltd., Tokyo (JP); National University Corporation Tokyo University of Agriculture and Technology, Tokyo (JP)

( * ) Notice: Subject to any disclaimer, the term of this patent is extended or adjusted under 35 U.S.C. 154(b) by 0 days.

(21) Appl. No.: 13/243,088

(22) Filed: Sep. 23, 2011

(65) Prior Publication Data
US 2012/0196350 A1 Aug. 2, 2012

(30) Foreign Application Priority Data
Feb. 2, 2011 (JP) ................................. 2011-020655

(51) Int. Cl.
*C12N 1/12* (2006.01)
*C12N 1/00* (2006.01)
*A62D 3/00* (2007.01)
*A62D 3/02* (2007.01)
*B09B 3/00* (2006.01)
*B09C 1/10* (2006.01)
*C02F 3/00* (2006.01)

(52) U.S. Cl.
USPC ..................... 435/252.1; 435/243; 435/262.5; 210/601

(58) Field of Classification Search
USPC ....................................................... 435/252.1
See application file for complete search history.

(56) References Cited

FOREIGN PATENT DOCUMENTS

| JP | 2001-269175 A | 10/2001 |
|---|---|---|
| JP | 2005-270970 A | 10/2005 |
| JP | 2006-042815 A | 2/2006 |
| JP | 2007-089560 A | 4/2007 |
| JP | 2007-104916 A | 4/2007 |
| JP | 2010-119339 A | 6/2010 |

OTHER PUBLICATIONS

X. Maymo-Gatell, et al., Reductive Dechlorination of Chlorinated Ethenes and 1,2-Dichloroethane by "*Dehalococcoides ethenogenes*" 195, Applied and Environmental Microbiology, Jul. 1999, pp. 3108-3113.

J. He, et al., "Detoxification of vinyl chloride to ethene coupled to growth of an anaerobic bacterium," Nature, Jul. 2003, pp. 62-65, vol. 424, www.nature.com/nature.

A. Cupples, et al., "Growth of a *Dehalococcoides*-Like Microorganism on Vinyl Chloride and cis-Dichloroethene an Electron Acceptors as Determined by Competitive PCR," Applied and Enviornmental Microbiology, Feb. 2003, pp. 953-959, vol. 69, No. 2.

(Continued)

*Primary Examiner* — Ruth Davis
*Assistant Examiner* — Sheridan Macauley
(74) *Attorney, Agent, or Firm* — Sughrue Mion, PLLC

(57) ABSTRACT

The bacterium that can perform complete dechlorination of trichloroethene, and the bacteria consortium containing the bacterium are provided, and the method to dechlorinate soils or ground water contaminated with trichloroethene using the bacterium is also provide.

4 Claims, 14 Drawing Sheets

(56) References Cited

OTHER PUBLICATIONS

J. He, et al., "Isoloation and characterization of *Dehalococcoides* sp. strain FL2, a trichloroethene (TCE)- and 1,2-dichloroethene-respiring anaerobe," Environmental Microbiology, 2005, pp. 1442-1450, vol. 7, No. 9.

Y. Sung, et al., "Quantitative PCR Confirms Purity of Strain GT, a Novel Trichloroethene-to-Ethene-Respiring *Dehalococcoides* Isolate," Applied and Environmental Microbiology, Mar. 2006, pp. 1980-1987, vol. 72, No. 3.

I. Utkin, et al., "Isoloation and Characterization of Desulfitobacterium dehalogenans gen. nov., sp. nov., an Anaerobic Bacterium Which Reductively Dechlorinates Chlorophenolic Compounds," International Journal of Systematic Bacteriology, Oct. 1994, pp. 612-619, vol. 44, No. 4.

J. Magnuson, et al., "Trichloroethene Reductive Dehalogenase from *Dehalococcoides ethenogenes*: Sequence of tceA and Substrate Range Characterization," Applied and Environmental Microbiology, Dec. 2000, pp. 5141-5147, vol. 66, No. 12.

R. Krajmalnik-Brown, et al., "Genetic Identification of a Putative Vinyl Chloride Reductase in *Dehalococcoides* sp. Strain BAV1," Applied and Environmental Microbiology, Oct. 2004, pp. 6347-6351, vol. 70, No. 10.

J. Muller, et al., "Molecular Indentification of the Catabolic Vinyl Chloride Reductase from *Dehalococcoides* sp. Strain VS and Its Environmental Distribution," Applied and Environmental Microbiology, Aug. 2004, pp. 4880-4888, vol. 70, No. 8.

Meeting Abstract of The 62nd Annual Meeting of The Society for Biotechnology, Japan (2010).

M. Kitajima, et al., "Analysis of consortium of cis-dichloroethene dechlorinating *Dehalococcoides* by Next Generation Sequencer," Meeting Abstract of the $62^{nd}$ Annual Meeting of the Society for Biotechnology, Japan; The Society for Biotechnology, Japan, Sep. 25, 2010, 1 page total.

M. Iwamoto, et al., "Development of consortium of cis-1, 2-dichlorothene dechlorination microbe for bioaugmentation," Meeting Abstract of the $62^{nd}$ Annual Meeting of the Society for Biotechnology, Japan the Society for Biotechnology, Japan, Sep. 25, 2010, 1 page total.

Meeting Abstract of The 62nd Annual Meeting of The Society for Biotechnology, Japan, Sep. 25, 2010, The Society of Biotechnology, Japan of c/o School Engineering Osaka University, 2-1, Yamadaoka, Suita-shi, Osaka-fu, http://www.sbj.or.jp.

SEQUENCE LISTING

<160> NUMBER OF SEQ ID NOS: 32

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
ctggagctaa tccccaaagc t                                          21

<210> SEQ ID NO 2
<211> LENGTH: 18
<212> TYPE: DNA
<213> ORGANISM: Artificial Sequence

```
<220> FEATURE:
<223> OTHER INFORMATION: Synthetic oligonucleotide

<400> SEQUENCE: 2
caacttcatg caggcggg                                                      18

<210> SEQ ID NO 3
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 3
cctcagttcg gatgc                                                         15

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 4
aaaagcactt ggctatcaag gac                                                23

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 5
ccaaaagcac caccaggtc                                                     19

<210> SEQ ID NO 6
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 6
ctatggcgac cgcagg                                                        16

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
ctcggctacc gaacggatt                                                     19

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
gggcaggagg attgacacat                                                    20
```

```
<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
cgcggtaata cgtaggaagc                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
ctctggtgtt cctcccgata                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
atacgcgagg aaccttaccc                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
ggcatcttta cgatggcagt                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
acaagcggtg gagcatgtgg                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
gtaaggttcc tcgcgtacca                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
```

```
tggggagcaa acaggattag                                                  20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
cgttgcatcg aattaaacca                                                  20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
gagcaaacag gattagatac                                                  20

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
acccaacatc tctacgacac g                                                21

<210> SEQ ID NO 19
<211> LENGTH: 1486
<212> TYPE: DNA
<213> ORGANISM: Dehalococcoides sp. ATV1

<400> SEQUENCE: 19
gctaactacg tgccagcagc cgcggtaata cgtaggaagc aagcgttatc cgatgaacgc      60
tagcggcgtg ccttatgcat gcaagtcgaa cggtcttaag caattaagat agtggcaaac     120
gggtgagtaa cgcgtaagta acctacctct aagtggggga tagcttcggg aaactgaagg     180
taataccgca tgtgatgggc tgacataagt cggttcatta aagccgcaag gtgcttggtg     240
aggggcttgc gtccgattag ctagttggtg gggtaatggc ctaccaaggc ttcgatcggt     300
agctggtctg agaggatgat cagccacact gggactgaga cacggcccag actcctacgg     360
gaggcagcag caaggaatct tgggcaatgg gcgaaagcct gacccagcaa cgccgcgtga     420
gggatgaagg ctttcgggtt gtaaacctct tttcacaggg aagaataatg acggtacctg     480
tgaataagc ttcggctaac tacgtgccag cagccgcggt aatacgtagg aagcaagcgt      540
tatccggatt tattgggcgt aaagtgagcg taggtggtct ttcaagttgg atgtgaaatt     600
tcccggctta accgggacgt gtcattcaat actgttggac tagagtacag caggagaaaa     660
cggaattccc ggtgtagtgg taaaatgcgt agatatcggg aggaacacca gaggcgaagg     720
cggttttcta ggttgtcact gacactgagg ctcgaaagcg tggggagcga acagaattag     780
atactctggt agtccacgcc ttaaactatg gacactaggt ataggagta  cgaccctct     840
ctgtgccgaa gctaacgctt taagtgtccc gcctggggag tacggtcgca aggctaaaac     900
tcaaaggaat tgacggggc ccgcacaagc agcggagcgt gtggtttaat tcgatgctac     960
acgaagaacc ttaccaagat ttgacatgca tgaagtagtg aaccgaaagg gaaacgacct    1020
```

```
gttaagtcag gagtttgcac aggtgctgca tggctgtcgt cagctcgtgc cgtgaggtgt    1080
ttggttaagt cctgcaacga gcgcaaccct tgttgctagt taaattttct agcgagactg    1140
ccccgcgaaa cggggaggaa ggtggggatg acgtcaagtc agcatggcct ttatatcttg    1200
ggctacacac acgctacaat ggacagaaca ataggttgca acagtgtgaa ctggagctaa    1260
tccccaaagc tgtcctcagt tcggattgca ggctgaaacc cgcctgcatg aagttggagt    1320
tgctagtaac cgcatatcag caaggtgcgg tgaatacgtt ctcgggcctt gtacacaccg    1380
cccgtcacgt catgaaagcc ggtaacactt gaagtcgatg tgccaaccgc aaggaggcag    1440
tcgccgaggg tgggactggt aattgggacg aagtcgtaac aaggta                   1486
```

<210> SEQ ID NO 20
<211> LENGTH: 1434
<212> TYPE: DNA
<213> ORGANISM: Dehalococcoides ethenogenes
<220> FEATURE:
<221> NAME/KEY: misc_feature
<222> LOCATION: (1344)..(1344)
<223> OTHER INFORMATION: n is a, c, g, or t

<400> SEQUENCE: 20

```
gatgaacgct agcggcgtgc cttatgcatg caagtcgaac ggtcttaagc aattaagata     60
gtggcaaacg ggtgagtaac gcgtaagtaa cctacctcta agtgggggat agcttcggga    120
aactgaaggt aataccgcat gtgatgggct gacataagtc ggttcattaa agccgcaagg    180
tgcttggtga ggggcttgcg tccgattagc tagttggtgg ggtaatggtc taccaaggct    240
tcgatcggta gctggtctga gaggatgatc agccacactg ggactgagac acgggccaga    300
ctcctacggg aggcagcagc aaggaatctt gggcaatggg cgaaagcctg acccagcaac    360
gccgcgtgag ggatgaaggc tttcggttg taaacctctt ttcacaggga agaataatga    420
cggtacctgt ggaataagct tcggctaact acgtgccagc agccgcggta atacgtaggg    480
aagcaagcgt tatccggatt tattgggcgt aaagtgagcg taggtggtct ttcaagttgg    540
atgtgaaatt tcccggctta accgggacgt gtcattcaat actgttggac tagagtacag    600
caggagaaaa cggaattccc ggtgtagtgg taaaatgcgt agatatcggg aggaacacca    660
gaggcgaagg cggttttcta ggttgtcact gacactgagg ctcgaaagcg tggggagcga    720
acagaattag atactctggt agtccacgcc ttaaactatg gacactaggt atagggagta    780
tcgaccctct ctgtgccgaa gctaacgctt taagtgtccc gcctggggag tacggtcgca    840
aggctaaaac tcaaaggaat tgacggggc cgcacaagc agcggagcgt gtggtttaat    900
tcgatgctac acgaagaact taccaagatt tgacatgcat gaagtagtga accgaaaggg    960
aaacgacctg ttaagtcagg agtttgcaca ggtgctgcat ggctgtcgtc agctcgtgcc   1020
gtgaggtgtt gggttaagtc ctgcaacgag cgcaaccttg ttgctagtta aattttctag   1080
cgagactgcc ccgcgaaacg gggaggaagg tgggatgac gtcaagtcag catggccttt   1140
atatcttggg ctacacacac gctacaatgg acagaacaat aggttgcaac agtgtgaact   1200
ggagctaatc cccaaagctg tcctcagttc ggattgcagg ctgaaacccg cctgcatgaa   1260
gttggagttg ctagtaaccg catatcagca aggtgcggtg aatacgttct cgggccttgt   1320
acacaccgcc cgtcacgtca tganagccgg taacacttga agtcgatgtg ccaaccgcaa   1380
ggaggcagtc gccgagggtg ggactggtaa ttgggacgaa gtcgtaacaa ggta         1434
```

<210> SEQ ID NO 21
<211> LENGTH: 1665

<212> TYPE: DNA
<213> ORGANISM: Dehalococcoides sp. ATV1

<400> SEQUENCE: 21

```
atgagtgaaa aatatcattc tacagtcaca aggcgtgatt tcatgaagag attaggtttg      60
gcaggagccg gtgcgggggc actgggtgcc gcagtacttg cagagaataa cctgccgcat     120
gagtttaaag atgttgatga cctgctgtca gcaggtaaaa cttagaggg tgaccacgct      180
aataaagtaa acaatgagcc atggtgggtt accacgcgtg atcatgagga tccaacctgt     240
aatatagatt ggagccttat aaaaagatac agcggttgga caaccaggg agcatacttc      300
ttacctgagg attacctgtc tccaacctat acaggtagaa gacatactat tgttgattca     360
tctctagaag taaaattaca gggtaaaaaa tactgcgata tgcctttat aaaatcaggc      420
atagactgga tgaaggaaaa tattgatcca gattatgacc ctggtgaact gggctatggc     480
gaccgcaggg aagatgccct aatatatgcc gccacgaatg gctcacataa ttgctgggag     540
aacccgcttt atggacgcta tgaaggttct aggcctatc tctctatgcg aaccatgaat      600
ggaataaacg gcttgcatga atttggtcac gcagatatca aaaccaccaa ctacccgaag     660
tgggagggta cgcctgaaga aacctgtta atcatgcgca ccgccgcgcg ctacttcggg      720
gcttcttccg ttggcgccat taagataacg gataacgtga agaaaatctt ctataccaaa     780
gcccagcccct ttatcctcgg gccttggtat acgattacaa atatggctga atacattgaa    840
tatccggtcc cagtagataa ttatgctata cccattgtgt ttgaagatgt tcctgcagac     900
cagggacact acagctacaa gcgcttggt ggtgatgata agatagtggt gcccaatgct      960
ctagagaata tcttccccta tactatcatg ctccctgaga aacgctttaa gtatgcacat    1020
agcgtaccta tggacccatg ctcttgtatt gcctatcccc tctttacaga ggctgaggca    1080
cgcattcagc acttcattgc aggccttggt tataactcaa tgggtggcgg agttgaagct    1140
tggggtccgg gcggtgcctt cggcaactta agtggccttg ggaacaatc acgcgtatca     1200
agcattattg agccccgcta cggctctaac accaagggtt ccctaaggat gcttacggac    1260
ctgcccccttg cccccaccaa gcctatagat gccggtatcc gtgagttctg taagacctgc    1320
ggcatctgtg ccgagcattg tcctaaccag gccatctcgc atgaagggcc acgctatgac    1380
tcaccttact gggataacgt cagcggctat gagggctggc accttgacta tcataagtgc    1440
attaactgta ccaactgtga gaccttctgc cccttcttca ctatgagcaa taactcctgg    1500
gtgcacaact tggtcaagtc cactgttgcc actacgcccg ttttttaacgg tttcttaag    1560
aatatggaag aagccttcgg ctacggcccg cgctactcac caagcaggga tgaatggtgg    1620
gcctcagaaa acccaatacg cggcgcaagc gtagatattt tttaa                    1665
```

<210> SEQ ID NO 22
<211> LENGTH: 554
<212> TYPE: PRT
<213> ORGANISM: Dehalococcoides sp. ATV1

<400> SEQUENCE: 22

```
Met Ser Glu Lys Tyr His Ser Thr Val Thr Arg Arg Asp Phe Met Lys
1               5                   10                  15

Arg Leu Gly Leu Ala Gly Ala Gly Ala Gly Ala Leu Gly Ala Ala Val
            20                  25                  30

Leu Ala Glu Asn Asn Leu Pro His Glu Phe Lys Asp Val Asp Asp Leu
        35                  40                  45

Leu Ser Ala Gly Lys Thr Leu Glu Gly Asp His Ala Asn Lys Val Asn
    50                  55                  60
```

-continued

Asn Glu Pro Trp Trp Val Thr Thr Arg Asp His Glu Asp Pro Thr Cys
 65                  70                  75                  80

Asn Ile Asp Trp Ser Leu Ile Lys Arg Tyr Ser Gly Trp Asn Asn Gln
             85                  90                  95

Gly Ala Tyr Phe Leu Pro Glu Asp Tyr Leu Ser Pro Tyr Thr Gly
            100                 105                 110

Arg Arg His Thr Ile Val Asp Ser Ser Leu Glu Val Lys Leu Gln Gly
            115                 120                 125

Lys Lys Tyr Cys Asp Ser Ala Phe Ile Lys Ser Gly Ile Asp Trp Met
130                 135                 140

Lys Glu Asn Ile Asp Pro Asp Tyr Asp Pro Gly Glu Leu Gly Tyr Gly
145                 150                 155                 160

Asp Arg Arg Glu Asp Ala Leu Ile Tyr Ala Ala Thr Asn Gly Ser His
            165                 170                 175

Asn Cys Trp Glu Asn Pro Leu Tyr Gly Arg Tyr Glu Gly Ser Arg Pro
            180                 185                 190

Tyr Leu Ser Met Arg Thr Met Asn Gly Ile Asn Gly Leu His Glu Phe
            195                 200                 205

Gly His Ala Asp Ile Lys Thr Thr Asn Tyr Pro Lys Trp Glu Gly Thr
210                 215                 220

Pro Glu Glu Asn Leu Leu Ile Met Arg Thr Ala Ala Arg Tyr Phe Gly
225                 230                 235                 240

Ala Ser Ser Val Gly Ala Ile Lys Ile Thr Asp Asn Val Lys Lys Ile
            245                 250                 255

Phe Tyr Thr Lys Ala Gln Pro Phe Ile Leu Gly Pro Trp Tyr Thr Ile
            260                 265                 270

Thr Asn Met Ala Glu Tyr Ile Glu Tyr Pro Val Pro Val Asp Asn Tyr
            275                 280                 285

Ala Ile Pro Ile Val Phe Glu Asp Val Pro Ala Asp Gln Gly His Tyr
            290                 295                 300

Ser Tyr Lys Arg Phe Gly Gly Asp Asp Lys Ile Val Val Pro Asn Ala
305                 310                 315                 320

Leu Glu Asn Ile Phe Thr Tyr Thr Ile Met Leu Pro Glu Lys Arg Phe
            325                 330                 335

Lys Tyr Ala His Ser Val Pro Met Asp Pro Cys Ser Cys Ile Ala Tyr
            340                 345                 350

Pro Leu Phe Thr Glu Ala Glu Ala Arg Ile Gln His Phe Ile Ala Gly
            355                 360                 365

Leu Gly Tyr Asn Ser Met Gly Gly Val Glu Ala Trp Gly Pro Gly
            370                 375                 380

Gly Ala Phe Gly Asn Leu Ser Gly Leu Gly Gln Ser Arg Val Ser
385                 390                 395                 400

Ser Ile Ile Glu Pro Arg Tyr Gly Ser Asn Thr Lys Gly Ser Leu Arg
            405                 410                 415

Met Leu Thr Asp Leu Pro Leu Ala Pro Thr Lys Pro Ile Asp Ala Gly
            420                 425                 430

Ile Arg Glu Phe Cys Lys Thr Cys Gly Ile Cys Ala Glu His Cys Pro
            435                 440                 445

Asn Gln Ala Ile Ser His Glu Gly Pro Arg Tyr Asp Ser Pro Tyr Trp
450                 455                 460

Asp Asn Val Ser Gly Tyr Glu Gly Trp His Leu Asp Tyr His Lys Cys
465                 470                 475                 480

Ile Asn Cys Thr Asn Cys Glu Thr Phe Cys Pro Phe Phe Thr Met Ser

```
                    485                 490                 495
Asn Asn Ser Trp Val His Asn Leu Val Lys Ser Thr Val Ala Thr Thr
            500                 505                 510

Pro Val Phe Asn Gly Phe Phe Lys Asn Met Glu Glu Ala Phe Gly Tyr
        515                 520                 525

Gly Pro Arg Tyr Ser Pro Ser Arg Asp Glu Trp Trp Ala Ser Glu Asn
    530                 535                 540

Pro Ile Arg Gly Ala Ser Val Asp Ile Phe
545                 550

<210> SEQ ID NO 23
<211> LENGTH: 1710
<212> TYPE: DNA
<213> ORGANISM: Dehalococcoides ethenogenes

<400> SEQUENCE: 23
ggtattttaa aagtatgagt gaaaaatatc attctacagt cacaaggcgt gatttcatga      60
agagattagg tttggcagga gccggtgcgg gggcactggg tgccgcagta cttgcagaga     120
ataacctgcc gcatgagttt aaagatgttg atgacctgct gtcagcaggt aaagcttttag    180 agggtgacca cgctaataaa gtaaacaatc atccatggtg ggttaccacg cgtgatcatg     240
aggatccaac ctgtaatata gattggagcc ttataaaaag atacagcggt tggaacaacc     300
agggagcata cttcttacct gaggattacc tgtctccaac ctatacaggt agaagacata     360
ccattgttga ttcaaaacta gaaatagaat tacagggtaa aaaataccgt gatagtgcct     420
ttataaaatc aggcatagac tggatgaagg aaaatattga tccagattat gaccctggtg     480
aactgggcta tggcgaccgc agggaagatg ccctaatata tgccgccacg aatggctcac     540
ataattgctg ggagaacccg ctttatggac gctatgaagg ttctaggcct tatctctcta     600
tgcgaaccat gaatgaata aacggcttgc atgaatttgg tcacgcagat atcaaaacca     660
ccaactaccc gaagtgggag ggtacgcctg aagagaacct gttaatcatg cgcaccgccg     720
cgcgctactt cggggcttct tccgttggcg ccattaagat aacggataac gtgaagaaaa     780
tcttctatgc caaagcccag ccctttttgcc tcgggccttg gtatacgatt acaaatatgg     840
ctgaatacat tgaatatccg gtcccagtag ataattatgc catacccatt gtgtttgaag     900
atatccctgc agaccagggg cattacagct acaaacgctt tggcggtgat gataagatag     960
cagtacccaa tgcactggat aacatcttca cctataccat catgctccct gagaagcgct    1020
ttaaatatgc acactctata cctatggacc catgctcttg tattgcctat ccctctttta    1080
cagaggttga ggcacgcatt cagcaattca ttgcaggcct tggctataac tcgatgggtg    1140
gtggagttga agcttgggt ccgggcagtg ccttcggcaa cttaagtggc cttggggaac    1200
aatcacgcgt atcaagcatt attgagcccc gctacggttc caacaccaag ggttccctaa    1260
ggatgcttac cgacctgcct cttgccccca ccaagcctat agatgccggt atccgcgagt    1320
tctgtaagac ctgcggcatc tgtgccgagc attgtcctac ccaagctatc tcgcatgaag    1380
ggccgcgcta tgactcacca cactgggatt gcgtaagcgg ttatgagggc tggcaccttg    1440
actatcacaa atgcattaac tgtaccatct gtgaggccgt ctgccccttc ttcactatga    1500
gcaataactc ctgggtgcac aacttggtca agtccactgt tgccactacg cccgttttta    1560
acggtttctt taagaatatg gaaggagcct tcggctacgg cccgcgctac tcaccaagca    1620
gggatgaatg gtgggcctca gaaaacccaa tacgcggcgc aagcgtagat attttttaag    1680
agaaaggatg gaatagatta ttatgggtgg                                     1710
```

<210> SEQ ID NO 24
<211> LENGTH: 554
<212> TYPE: PRT
<213> ORGANISM: Dehalococcoides ethenogenes

<400> SEQUENCE: 24

```
Met Ser Glu Lys Tyr His Ser Thr Val Thr Arg Arg Asp Phe Met Lys
1               5                   10                  15

Arg Leu Gly Leu Ala Gly Ala Gly Ala Leu Gly Ala Ala Val
            20                  25                  30

Leu Ala Glu Asn Asn Leu Pro His Glu Phe Lys Asp Val Asp Asp Leu
            35                  40                  45

Leu Ser Ala Gly Lys Ala Leu Glu Gly Asp His Ala Asn Lys Val Asn
50                  55                  60

Asn His Pro Trp Trp Val Thr Thr Arg Asp His Glu Asp Pro Thr Cys
65                  70                  75                  80

Asn Ile Asp Trp Ser Leu Ile Lys Arg Tyr Ser Gly Trp Asn Asn Gln
                85                  90                  95

Gly Ala Tyr Phe Leu Pro Glu Asp Tyr Leu Ser Pro Thr Tyr Thr Gly
            100                 105                 110

Arg Arg His Thr Ile Val Asp Ser Lys Leu Glu Ile Glu Leu Gln Gly
            115                 120                 125

Lys Lys Tyr Arg Asp Ser Ala Phe Ile Lys Ser Gly Ile Asp Trp Met
130                 135                 140

Lys Glu Asn Ile Asp Pro Asp Tyr Asp Pro Gly Glu Leu Gly Tyr Gly
145                 150                 155                 160

Asp Arg Arg Glu Asp Ala Leu Ile Tyr Ala Ala Thr Asn Gly Ser His
                165                 170                 175

Asn Cys Trp Glu Asn Pro Leu Tyr Gly Arg Tyr Glu Gly Ser Arg Pro
            180                 185                 190

Tyr Leu Ser Met Arg Thr Met Asn Gly Ile Asn Gly Leu His Glu Phe
            195                 200                 205

Gly His Ala Asp Ile Lys Thr Thr Asn Tyr Pro Lys Trp Glu Gly Thr
210                 215                 220

Pro Glu Glu Asn Leu Leu Ile Met Arg Thr Ala Ala Arg Tyr Phe Gly
225                 230                 235                 240

Ala Ser Ser Val Gly Ala Ile Lys Ile Thr Asp Asn Val Lys Lys Ile
                245                 250                 255

Phe Tyr Ala Lys Ala Gln Pro Phe Cys Leu Gly Pro Trp Tyr Thr Ile
            260                 265                 270

Thr Asn Met Ala Glu Tyr Ile Glu Tyr Pro Val Pro Val Asp Asn Tyr
275                 280                 285

Ala Ile Pro Ile Val Phe Glu Asp Ile Pro Ala Asp Gln Gly His Tyr
            290                 295                 300

Ser Tyr Lys Arg Phe Gly Gly Asp Lys Ile Ala Val Pro Asn Ala
305                 310                 315                 320

Leu Asp Asn Ile Phe Thr Tyr Thr Ile Met Leu Pro Glu Lys Arg Phe
                325                 330                 335

Lys Tyr Ala His Ser Ile Pro Met Asp Pro Cys Ser Cys Ile Ala Tyr
            340                 345                 350

Pro Leu Phe Thr Glu Val Glu Ala Arg Ile Gln Gln Phe Ile Ala Gly
            355                 360                 365

Leu Gly Tyr Asn Ser Met Gly Gly Gly Val Glu Ala Trp Gly Pro Gly
370                 375                 380
```

```
Ser Ala Phe Gly Asn Leu Ser Gly Leu Gly Glu Gln Ser Arg Val Ser
385                 390                 395                 400

Ser Ile Ile Glu Pro Arg Tyr Gly Ser Asn Thr Lys Gly Ser Leu Arg
            405                 410                 415

Met Leu Thr Asp Leu Pro Leu Ala Pro Thr Lys Pro Ile Asp Ala Gly
        420                 425                 430

Ile Arg Glu Phe Cys Lys Thr Cys Gly Ile Cys Ala Glu His Cys Pro
    435                 440                 445

Thr Gln Ala Ile Ser His Glu Gly Pro Arg Tyr Asp Ser Pro His Trp
450                 455                 460

Asp Cys Val Ser Gly Tyr Glu Gly Trp His Leu Asp Tyr His Lys Cys
465                 470                 475                 480

Ile Asn Cys Thr Ile Cys Glu Ala Val Cys Pro Phe Phe Thr Met Ser
            485                 490                 495

Asn Asn Ser Trp Val His Asn Leu Val Lys Ser Thr Val Ala Thr Thr
        500                 505                 510

Pro Val Phe Asn Gly Phe Phe Lys Asn Met Glu Gly Ala Phe Gly Tyr
    515                 520                 525

Gly Pro Arg Tyr Ser Pro Ser Arg Asp Glu Trp Ala Ser Glu Asn
530                 535                 540

Pro Ile Arg Gly Ala Ser Val Asp Ile Phe
545                 550

<210> SEQ ID NO 25
<211> LENGTH: 1551
<212> TYPE: DNA
<213> ORGANISM: Dehalococcoides sp. ATV1

<400> SEQUENCE: 25
atgcataatt tccattgtac gataagtagg cgagatttta tgaagggatt ggggttagcg     60
ggagcaggga taggtgccgc gacttcagtt atgccgaatt tcacgactt ggatgaagta    120 atttctgctg ctagtgccga aaccagttct tgtcgggta atctcttaa taattttcct    180 tggtatgtga agaaaggga ttttgaaaat cctaccattg atatagattg gtctatactt    240
gcgcgtcatg acggttacaa tcatcaggga gcctattggg gacctgtacc tgcaaatgga    300
tatgataaaa ggtatcctga tcccgcggac cagtgtctta ctctaccaga aagagagat    360 ctttatttag cgtgggcaaa acagcaattt cctgactggg aaccaggaat taatggccat    420
gggccaacaa gggacgaagc tttatggttt gcctcaagta caggtggtct cggtaggtat    480
agaattcctg gtacccagca aatgatgtcc acaatgcgtc ttgacgggtc tactggtggt    540
tggggttatt acaatctacc accggcagca gtctggggag ggaaataccc aaggtgggaa    600
ggaactcctg aagaaaatac gttgatgatg cgaactgttt gtcaattttt tggttactcc    660
agtataggtg taatgccaat caccagcaat acaagaagc tttttttga aaagcaaata    720 cctttccaat ttacccctgg agatcccggt gtatttgggg gaacgggaaa tgtgcagttt    780
gatgtcccgc tgccaaagac acctgttcca atagtctggg aggaagtcga taagggtat    840 tataatgacc agaaaattgt aatacccaat aaggctaact gggtattaac aatgacaatg    900 ccttaccag aagatcgttt taaacgttct ctagggtggt catgtgacgc ttcaagtatg    960
attgcctatc ctcagatggc ttttaatgga ggccgagttc agactttttt aaaagcactt   1020
ggctatcaag acttggtgg cgacatggct atgtgggac ctggtggtgc ttttggagtt   1080
atgagtggtc tttccgaaca aggtcgtgtt gctaatgaaa tcagcccaa atacggttcg   1140 gcaactaagg gctctaatcg attagtttgt gatttgccca tggttccgac caagccaatt   1200
```

```
gatgctggca tacacaaatt ctgtgaaacg tgtggcattt gtacaacagt ttgtccctca  1260
aatgctatcc aggtaggtcc tccacaatgg agtaataatc ggtgggataa taccccctggt  1320 tatcttggtt atcgacttaa ctggggtaga tgtgttcttt gtacaaactg tgagacctat  1380
tgcccatttt ttaacatgac taatggttct ttgattcata acgtagtcag atccacagtt  1440
gcagctacac cggtttttaa ttcattttc cgccaaatgg aacatacatt tggatatggt  1500
atgaaagatg atttaaacga ttggtggaat caatcacaca agccttggta a  1551
```

<210> SEQ ID NO 26
<211> LENGTH: 516
<212> TYPE: PRT
<213> ORGANISM: Dehalococcoides sp. ATV1

<400> SEQUENCE: 26

```
Met His Asn Phe His Cys Thr Ile Ser Arg Arg Asp Phe Met Lys Gly
1               5                   10                  15

Leu Gly Leu Ala Gly Ala Gly Ile Gly Ala Ala Thr Ser Val Met Pro
            20                  25                  30

Asn Phe His Asp Leu Asp Glu Val Ile Ser Ala Ala Ser Ala Glu Thr
        35                  40                  45

Ser Ser Leu Ser Gly Lys Ser Leu Asn Asn Phe Pro Trp Tyr Val Lys
    50                  55                  60

Glu Arg Asp Phe Glu Asn Pro Thr Ile Asp Ile Asp Trp Ser Ile Leu
65                  70                  75                  80

Ala Arg His Asp Gly Tyr Asn His Gln Gly Ala Tyr Trp Gly Pro Val
                85                  90                  95

Pro Ala Asn Gly Tyr Asp Lys Arg Tyr Pro Asp Pro Ala Asp Gln Cys
            100                 105                 110

Leu Thr Leu Pro Glu Lys Arg Asp Leu Tyr Leu Ala Trp Ala Lys Gln
        115                 120                 125

Gln Phe Pro Asp Trp Glu Pro Gly Ile Asn Gly His Gly Pro Thr Arg
    130                 135                 140

Asp Glu Ala Leu Trp Phe Ala Ser Ser Thr Gly Gly Leu Gly Arg Tyr
145                 150                 155                 160

Arg Ile Pro Gly Thr Gln Gln Met Met Ser Thr Met Arg Leu Asp Gly
                165                 170                 175

Ser Thr Gly Gly Trp Gly Tyr Tyr Asn Leu Pro Pro Ala Ala Val Trp
            180                 185                 190

Gly Gly Lys Tyr Pro Arg Trp Glu Gly Thr Pro Glu Asn Thr Leu
        195                 200                 205

Met Met Arg Thr Val Cys Gln Phe Gly Tyr Ser Ser Ile Gly Val
    210                 215                 220

Met Pro Ile Thr Ser Asn Thr Lys Lys Leu Phe Phe Glu Lys Gln Ile
225                 230                 235                 240

Pro Phe Gln Phe Thr Pro Gly Asp Pro Gly Val Phe Gly Gly Thr Gly
                245                 250                 255

Asn Val Gln Phe Asp Val Pro Leu Pro Lys Thr Pro Val Pro Ile Val
            260                 265                 270

Trp Glu Glu Val Asp Lys Gly Tyr Tyr Asn Asp Gln Lys Ile Val Ile
        275                 280                 285

Pro Asn Lys Ala Asn Trp Val Leu Thr Met Thr Met Pro Leu Pro Glu
    290                 295                 300

Asp Arg Phe Lys Arg Ser Leu Gly Trp Ser Cys Asp Ala Ser Ser Met
305                 310                 315                 320
```

Ile Ala Tyr Pro Gln Met Ala Phe Asn Gly Gly Arg Val Gln Thr Phe
            325                 330                 335

Leu Lys Ala Leu Gly Tyr Gln Gly Leu Gly Gly Asp Met Ala Met Trp
            340                 345                 350

Gly Pro Gly Gly Ala Phe Gly Val Met Ser Gly Leu Ser Glu Gln Gly
            355                 360                 365

Arg Val Ala Asn Glu Ile Ser Pro Lys Tyr Gly Ser Ala Thr Lys Gly
            370                 375                 380

Ser Asn Arg Leu Val Cys Asp Leu Pro Met Val Pro Thr Lys Pro Ile
385                 390                 395                 400

Asp Ala Gly Ile His Lys Phe Cys Glu Thr Cys Gly Ile Cys Thr Thr
            405                 410                 415

Val Cys Pro Ser Asn Ala Ile Gln Val Gly Pro Pro Gly Trp Ser Asn
            420                 425                 430

Asn Arg Trp Asp Asn Thr Pro Gly Tyr Leu Gly Tyr Arg Leu Asn Trp
            435                 440                 445

Gly Arg Cys Val Leu Cys Thr Asn Cys Glu Thr Tyr Cys Pro Phe Phe
            450                 455                 460

Asn Met Thr Asn Gly Ser Leu Ile His Asn Val Val Arg Ser Thr Val
465                 470                 475                 480

Ala Ala Thr Pro Val Phe Asn Ser Phe Phe Arg Gln Met Glu His Thr
            485                 490                 495

Phe Gly Tyr Gly Met Lys Asp Asp Leu Asn Asp Trp Trp Asn Gln Ser
            500                 505                 510

His Lys Pro Trp
        515

<210> SEQ ID NO 27
<211> LENGTH: 1551
<212> TYPE: DNA
<213> ORGANISM: Dehalococcoides sp. BAV1

<400> SEQUENCE: 27
atgcataatt tccattgtac gataagtagg cgagattttta tgaagggatt ggggttagcg    60
ggagcaggga taggtgccgc gacttcagtt atgccgaatt tcacgacttt ggatgaagta   120
atttctgctg ctagtgccga aaccagttct ttgtcgggta atctcttaa taattttcct   180 tggtatgtga agaaaggga ttttgaaaat cctaccattg atatagattg gtctatactt   240
gcgcgtaatg acggttacaa tcatcaggga gcctattggg gacctgtacc tgaaaatgga   300
gatgataaaa ggtatcctga tcccgcggac cagtgtctta ctctaccaga aagagagat   360 ctttatttag cgtgggcaaa acagcaattt cctgactggg aaccaggaat taatggccat   420
gggccaacaa gggacgaagc tttatggttt gcctcaagta caggtggtat cggtaggtat   480
agaattcctg gtacccagca aatgatgtcc acaatgcgtc ttgacgggtc tactggtggt   540
tggggttatt tcaatcaacc accggcagca gtctggggag ggaaataccc aaggtgggaa   600
ggaactcctg aagagaatac gttgatgatg cgaactgttt gtcaattttt tggttactcc   660
agtataggtg taatgccaat caccagcaat acaaagaagc ttttttttga aaagcaaata   720
cctttccaat ttatggctgg agatcccggt gtatttgggg gaacgggaaa tgtgcagttt   780
gatgtcccgc tgccaaagac acctgttcca atagtctggg aggaagtcga taagggtat   840 tataatgacc agaaaattgt aatacccaat aaggctaact gggtattaac aatgacaatg   900
cctttaccag aagatcgttt taaacgttct ctagggtggt cacttgacgc ttcaagtatg   960

-continued

```
attgcctatc ctcagatggc ttttaatgga ggccgagttc agactttttt aaaagcactt    1020
ggctatcaag gacttggtgg cgacgtggct atgtggggac ctggtggtgc ttttggagtt    1080
atgagtggtc tttccgaaca aggtcgtgct gctaatgaaa tcagccccaa atacggttcg    1140
gcaactaagg gctctaatcg attagtttgt gatttgccca tggttccgac caagccaatt    1200
gatgctggca tacacaaatt ctgtgaaacg tgtggcattt gtacaacagt tgtccctca    1260 aatgctatcc aggtaggtcc tccacaatgg agtaataatc ggtgggataa tacccctggt    1320
tatcttggtt atcgacttaa ctggggtaga tgtgttcttt gtacaaactg tgagacctat    1380
tgcccatttt ttaacatgac taatggttct tgattcata acgtagtcag atccacagtt    1440
gcagctacac cggtttttaa ttcattttc cgccaaatgg aacatacatt tggatatggt    1500
atgaaagatg atttaaacga ttggtggaat caatcacaca agccttggta a             1551
```

<210> SEQ ID NO 28
<211> LENGTH: 516
<212> TYPE: PRT
<213> ORGANISM: Dehalococcoides sp. BAV1

<400> SEQUENCE: 28

```
Met His Asn Phe His Cys Thr Ile Ser Arg Arg Asp Phe Met Lys Gly
1               5                   10                  15

Leu Gly Leu Ala Gly Ala Gly Ile Gly Ala Ala Thr Ser Val Met Pro
            20                  25                  30

Asn Phe His Asp Leu Asp Glu Val Ile Ser Ala Ala Ser Ala Glu Thr
        35                  40                  45

Ser Ser Leu Ser Gly Lys Ser Leu Asn Asn Phe Pro Trp Tyr Val Lys
    50                  55                  60

Glu Arg Asp Phe Glu Asn Pro Thr Ile Asp Ile Asp Trp Ser Ile Leu
65                  70                  75                  80

Ala Arg Asn Asp Gly Tyr Asn His Gln Gly Ala Tyr Trp Gly Pro Val
                85                  90                  95

Pro Glu Asn Gly Asp Asp Lys Arg Tyr Pro Asp Pro Ala Asp Gln Cys
            100                 105                 110

Leu Thr Leu Pro Glu Lys Arg Asp Leu Tyr Leu Ala Trp Ala Lys Gln
        115                 120                 125

Gln Phe Pro Asp Trp Glu Pro Gly Ile Asn Gly His Gly Pro Thr Arg
    130                 135                 140

Asp Glu Ala Leu Trp Phe Ala Ser Ser Thr Gly Gly Ile Gly Arg Tyr
145                 150                 155                 160

Arg Ile Pro Gly Thr Gln Gln Met Met Ser Thr Met Arg Leu Asp Gly
                165                 170                 175

Ser Thr Gly Gly Trp Gly Tyr Phe Asn Gln Pro Pro Ala Ala Val Trp
            180                 185                 190

Gly Gly Lys Tyr Pro Arg Trp Glu Gly Thr Pro Glu Glu Asn Thr Leu
        195                 200                 205

Met Met Arg Thr Val Cys Gln Phe Gly Tyr Ser Ser Ile Gly Val
    210                 215                 220

Met Pro Ile Thr Ser Asn Thr Lys Lys Leu Phe Glu Lys Gln Ile
225                 230                 235                 240

Pro Phe Gln Phe Met Ala Gly Asp Pro Gly Val Phe Gly Gly Thr Gly
                245                 250                 255

Asn Val Gln Phe Asp Val Pro Leu Pro Lys Thr Pro Val Pro Ile Val
            260                 265                 270

Trp Glu Glu Val Asp Lys Gly Tyr Tyr Asn Asp Gln Lys Ile Val Ile
```

|     |     |     |     | 275 |     |     |     | 280 |     |     |     | 285 |     |     |
| --- | --- | --- | --- | --- | --- | --- | --- | --- | --- | --- | --- | --- | --- | --- |
| Pro | Asn | Lys | Ala | Asn | Trp | Val | Leu | Thr | Met | Thr | Met | Pro | Leu | Pro | Glu |
|     | 290 |     |     |     | 295 |     |     |     | 300 |     |     |     |     |     |     |
| Asp | Arg | Phe | Lys | Arg | Ser | Leu | Gly | Trp | Ser | Leu | Asp | Ala | Ser | Ser | Met |
| 305 |     |     |     |     | 310 |     |     |     |     | 315 |     |     |     |     | 320 |
| Ile | Ala | Tyr | Pro | Gln | Met | Ala | Phe | Asn | Gly | Gly | Arg | Val | Gln | Thr | Phe |
|     |     |     |     | 325 |     |     |     |     | 330 |     |     |     |     | 335 |     |
| Leu | Lys | Ala | Leu | Gly | Tyr | Gln | Gly | Leu | Gly | Gly | Asp | Val | Ala | Met | Trp |
|     |     |     | 340 |     |     |     |     | 345 |     |     |     |     | 350 |     |     |
| Gly | Pro | Gly | Gly | Ala | Phe | Gly | Val | Met | Ser | Gly | Leu | Ser | Glu | Gln | Gly |
|     |     | 355 |     |     |     |     | 360 |     |     |     |     | 365 |     |     |     |
| Arg | Ala | Ala | Asn | Glu | Ile | Ser | Pro | Lys | Tyr | Gly | Ser | Ala | Thr | Lys | Gly |
|     | 370 |     |     |     |     | 375 |     |     |     |     | 380 |     |     |     |     |
| Ser | Asn | Arg | Leu | Val | Cys | Asp | Leu | Pro | Met | Val | Pro | Thr | Lys | Pro | Ile |
| 385 |     |     |     |     | 390 |     |     |     |     | 395 |     |     |     |     | 400 |
| Asp | Ala | Gly | Ile | His | Lys | Phe | Cys | Glu | Thr | Cys | Gly | Ile | Cys | Thr | Thr |
|     |     |     |     | 405 |     |     |     |     | 410 |     |     |     |     | 415 |     |
| Val | Cys | Pro | Ser | Asn | Ala | Ile | Gln | Val | Gly | Pro | Pro | Gln | Trp | Ser | Asn |
|     |     |     | 420 |     |     |     |     | 425 |     |     |     |     | 430 |     |     |
| Asn | Arg | Trp | Asp | Asn | Thr | Pro | Gly | Tyr | Leu | Gly | Tyr | Arg | Leu | Asn | Trp |
|     |     | 435 |     |     |     |     | 440 |     |     |     |     | 445 |     |     |     |
| Gly | Arg | Cys | Val | Leu | Cys | Thr | Asn | Cys | Glu | Thr | Tyr | Cys | Pro | Phe | Phe |
|     | 450 |     |     |     |     | 455 |     |     |     |     | 460 |     |     |     |     |
| Asn | Met | Thr | Asn | Gly | Ser | Leu | Ile | His | Asn | Val | Val | Arg | Ser | Thr | Val |
| 465 |     |     |     |     | 470 |     |     |     |     | 475 |     |     |     |     | 480 |
| Ala | Ala | Thr | Pro | Val | Phe | Asn | Ser | Phe | Phe | Arg | Gln | Met | Glu | His | Thr |
|     |     |     |     | 485 |     |     |     |     | 490 |     |     |     |     | 495 |     |
| Phe | Gly | Tyr | Gly | Met | Lys | Asp | Asp | Leu | Asn | Asp | Trp | Trp | Asn | Gln | Ser |
|     |     |     | 500 |     |     |     |     | 505 |     |     |     |     | 510 |     |     |
| His | Lys | Pro | Trp |     |     |     |     |     |     |     |     |     |     |     |     |
|     |     | 515 |     |     |     |     |     |     |     |     |     |     |     |     |     |

<210> SEQ ID NO 29
<211> LENGTH: 1557
<212> TYPE: DNA
<213> ORGANISM: Dehalococcoides sp. ATV1

<400> SEQUENCE: 29

```
atgagtaaat tcataaaaac gattagccgc cgagatttca tgaaaggact aggattagcc      60
ggggggcggta ttggtgttgc ggcgtcagct ccggttttc atgacattga tgaatttgtt     120
tcaagcgaag caattctac taaagatcaa ccttggtacg ttaagcatcg agagcatttt     180
gaccctacga ttacagttga ctgggatatt tttgatagat atgacgggta tcagcataag     240
ggtgtctatg aaggccctcc agatgctccc tttacatcat gggcaatag gcttcagatg     300
agaatgtcag gtgaagagca aaagaagcga attttggccg ctaaaaaaga gaggttccct     360
ggttgggacg tgggttaca cgggagaggg gatcagcggg cggatgcact atttttacgca    420
gtaactcaac catttcctgg tagtggtgag gaagggcacg gactattcca accttatcct    480
gatcaacccg gtaagtttta cgcgagatgg ggtttgtatg gtccgccaca tgattcagcg    540
ccacctgatg gagcgtacc aaaatgggag agtactccag aagacaattt tctaatgctg    600
agggcagctg caaatatttt tggtgctggt ggcgttggtg ctcttaacct ggcagatccc    660
aaatgcaaaa aactaatata taagaaagct cagccgatga ctctaggaaa aggaacatac    720
agtgaaatag gtggaccagg aatgatcgat gcaaaatttt atcccaaggt tcctgaccat    780
```

```
gccgtaccta ttaactttaa ggaagcggat tatagctact acaatgatgc agagtgggtt      840
attccaacaa agtgtgaatc cattttcact ttcaccctac ctcaaccaca agaactcaat      900
aagaggacgg gtggtatagc aggtgctgga tcatatactg tatacaaaga tttcgctagg      960
gtaggcactt tagtccaatt gtttattaag aatctaggtt atcacgcttt atattggcca     1020
attggatggg gaccgggtgg ttgctttacc acttttgacg ggcaaggtga acagggtaga     1080
acaggtgctg ctatccattg gaagtttggt tcttcacaac gtggttctga cagagtagta     1140
actgatttac cgatagctcc taccccgcca attgatgcag gtatgtttga gttttgcaaa     1200
acctgttata tatgccgtga cgtttgcgtc tctgggggtg tgcaccaaga agacgaacca     1260
acttgggatt caggtaattg gtggaatgta caaggatatc tcggctaccg aacggattgg     1320
agtggttgcc ataaccagtg cggtatgtgt caaccctcct gccctttac ttatttaggt      1380 ttggaaaatg cttcattagt gcacaaaata gtaaaggtg ttgttgctaa cacgactgtt      1440
tttaatagtt tttttaccaa tatggagaaa gcattaggat atggtgattt aaccatggaa     1500
aattctaact ggtggaaaga agaaggaccg atatacggct ttgatcccgg tacttag       1557
```

<210> SEQ ID NO 30
<211> LENGTH: 518
<212> TYPE: PRT
<213> ORGANISM: Dehalococcoides sp. ATV1

<400> SEQUENCE: 30

```
Met Ser Lys Phe His Lys Thr Ile Ser Arg Arg Asp Phe Met Lys Gly
 1               5                  10                  15

Leu Gly Leu Ala Gly Gly Gly Ile Gly Val Ala Ala Ser Ala Pro Val
            20                  25                  30

Phe His Asp Ile Asp Glu Phe Val Ser Ser Glu Ala Asn Ser Thr Lys
        35                  40                  45

Asp Gln Pro Trp Tyr Val Lys His Arg Glu His Phe Asp Pro Thr Ile
    50                  55                  60

Thr Val Asp Trp Asp Ile Phe Asp Arg Tyr Asp Gly Tyr Gln His Lys
65                  70                  75                  80

Gly Val Tyr Glu Gly Pro Pro Asp Ala Pro Phe Thr Ser Trp Gly Asn
                85                  90                  95

Arg Leu Gln Met Arg Met Ser Gly Glu Glu Lys Lys Arg Ile Leu
            100                 105                 110

Ala Ala Lys Lys Glu Arg Phe Pro Gly Trp Asp Gly Gly Leu His Gly
        115                 120                 125

Arg Gly Asp Gln Arg Ala Asp Ala Leu Phe Tyr Ala Val Thr Gln Pro
    130                 135                 140

Phe Pro Gly Ser Gly Glu Glu Gly His Gly Leu Phe Gln Pro Tyr Pro
145                 150                 155                 160

Asp Gln Pro Gly Lys Phe Tyr Ala Arg Trp Gly Leu Tyr Gly Pro Pro
                165                 170                 175

His Asp Ser Ala Pro Pro Asp Gly Ser Val Pro Lys Trp Glu Ser Thr
            180                 185                 190

Pro Glu Asp Asn Phe Leu Met Leu Arg Ala Ala Ala Lys Tyr Phe Gly
        195                 200                 205

Ala Gly Gly Val Gly Ala Leu Asn Leu Ala Asp Pro Lys Cys Lys Lys
    210                 215                 220

Leu Ile Tyr Lys Lys Ala Gln Pro Met Thr Leu Gly Lys Gly Thr Tyr
225                 230                 235                 240
```

```
Ser Glu Ile Gly Gly Pro Gly Met Ile Asp Ala Lys Phe Tyr Pro Lys
                245                 250                 255

Val Pro Asp His Ala Val Pro Ile Asn Phe Lys Glu Ala Asp Tyr Ser
            260                 265                 270

Tyr Tyr Asn Asp Ala Glu Trp Val Ile Pro Thr Lys Cys Glu Ser Ile
        275                 280                 285

Phe Thr Phe Thr Leu Pro Gln Pro Gln Glu Leu Asn Lys Arg Thr Gly
    290                 295                 300

Gly Ile Ala Gly Ala Gly Ser Tyr Thr Val Tyr Lys Asp Phe Ala Arg
305                 310                 315                 320

Val Gly Thr Leu Val Gln Leu Phe Ile Lys Asn Leu Gly Tyr His Ala
                325                 330                 335

Leu Tyr Trp Pro Ile Gly Trp Pro Gly Gly Cys Phe Thr Thr Phe
            340                 345                 350

Asp Gly Gln Gly Glu Gln Gly Arg Thr Gly Ala Ala Ile His Trp Lys
        355                 360                 365

Phe Gly Ser Ser Gln Arg Gly Ser Asp Arg Val Val Thr Asp Leu Pro
    370                 375                 380

Ile Ala Pro Thr Pro Ile Asp Ala Gly Met Phe Glu Phe Cys Lys
385                 390                 395                 400

Thr Cys Tyr Ile Cys Arg Asp Val Cys Val Ser Gly Gly Val His Gln
                405                 410                 415

Glu Asp Glu Pro Thr Trp Asp Ser Gly Asn Trp Asn Val Gln Gly
            420                 425                 430

Tyr Leu Gly Tyr Arg Thr Asp Trp Ser Gly Cys His Asn Gln Cys Gly
        435                 440                 445

Met Cys Gln Pro Ser Cys Pro Phe Thr Tyr Leu Gly Leu Glu Asn Ala
    450                 455                 460

Ser Leu Val His Lys Ile Val Lys Gly Val Val Ala Asn Thr Thr Val
465                 470                 475                 480

Phe Asn Ser Phe Phe Thr Asn Met Glu Lys Ala Leu Gly Tyr Gly Asp
                485                 490                 495

Leu Thr Met Glu Asn Ser Asn Trp Trp Lys Glu Glu Gly Pro Ile Tyr
            500                 505                 510

Gly Phe Asp Pro Gly Thr
        515

<210> SEQ ID NO 31
<211> LENGTH: 1710
<212> TYPE: DNA
<213> ORGANISM: Dehalococcoides spDVS

<400> SEQUENCE: 31
ggaaacgctt atggatattt ggcgttcagg aaagactgaa tggctctagg gaaagaccta      60
aatatatctt taggataaat ttatgagtaa atttcataaa acgattagcc gccgagattt     120
catgaaagga ctaggattag ccggggcagg cataggcgct gttgcggcgt cagctccggt     180
ttttcatgac attgatgaac ttgtttcaag cgaagcaaat tctactaaag atcaaccttg     240
gtacgttaag catcgagagc attttgaccc tacgattaca gttgactggg atattttttga    300 tagatatgac gggtatcagc ataagggtgt ctatgaaggc cctccagatg ctcccttttac    360 atcatggggc aataggcttc aggtgagaat gtcaggtgaa gagcaaaaga agcgaatttt    420
ggccgctaaa aaagagaggt tccctggttg gacggtggg ttacacggga gaggggatca    480
gcgggcggat gcactatttt acgcagtaac tcaaccattt cctggtagtg gtgaggaagg    540
```

```
gcacggacta ttccaacctt atcctgatca acccggtaag ttttacgcga gatggggttt      600
gtatggtccg ccacatgatt cagcgccacc tgatgggagc gtaccaaaat gggagggtac      660
tccagaagac aatttctaa tgctgagggc agctgcaaaa tattttggtg ctggtggcgt       720
tggtgctctt aacctggcag atcccaaatg caaaaaacta atatataaga aagctcagcc      780
gatgactcta ggaaaaggaa catacagtga ataggtgga ccaggaatga tcgatgcaaa       840
aatttatccc aaggttcctg accatgccgt acctattaac tttaaggaag cggattatag      900
ctactacaat gatgcagagt gggttattcc aacaaagtgt gaatccattt tcactttcac      960
cctacctcaa ccacaagaac tcaataagag gacgggtggt atagcaggtg ctggatcata     1020
tactgtatac aaagatttcg ctagggtagg cactttagtc caaatgttta ttaagtatct     1080
aggttatcac gctttatatt ggccaattgg atggggaccg ggtggttgct ttaccacttt     1140
tgacgggcaa ggtgaacagg gtagaacagg tgctgctatc cattggaagt ttggttcttc     1200
acaacgtggt tctgaaagag taataactga tttaccgata gctcctaccc cgccaattga     1260
tgcaggtatg tttgagtttt gcaaaacctg ttatatatgc cgtgacgttt gcgtctctgg     1320
gggtgtgcac caagaagacg aaccaacttg ggattcaggt aattggtgga atgtacaagg     1380
atatctcggc taccgaacgg attggagtgg ttgccataac cagtgcggta tgtgtcaatc     1440
ctcctgccct tttacttatt taggtttgga aaatgcttca ttagtgcaca aaatagtaaa     1500
aggtgttgtt gctaacacga ctgtttttaa tagttttttt accaatatgg agaaagcatt     1560
aggatatggt gatttaacca tggaaaattc taactggtgg aaagaagaag gaccgatata     1620
cggctttgat cccggtactt agaaatagat actaaattcg atagaaaata aaggaaattg     1680
aaatggatgc tatatatttt ttcttaacaa                                      1710
```

<210> SEQ ID NO 32
<211> LENGTH: 519
<212> TYPE: PRT
<213> ORGANISM: Dehalococcoides spDVS

<400> SEQUENCE: 32

Met Ser Lys Phe His Lys Thr Ile Ser Arg Arg Asp Phe Met Lys Gly
1               5                   10                  15

Leu Gly Leu Ala Gly Ala Gly Ile Gly Ala Val Ala Ala Ser Ala Pro
            20                  25                  30

Val Phe His Asp Ile Asp Glu Leu Val Ser Ser Glu Ala Asn Ser Thr
        35                  40                  45

Lys Asp Gln Pro Trp Tyr Val Lys His Arg Glu His Phe Asp Pro Thr
    50                  55                  60

Ile Thr Val Asp Trp Asp Ile Phe Asp Arg Tyr Asp Gly Tyr Gln His
65                  70                  75                  80

Lys Gly Val Tyr Glu Gly Pro Pro Asp Ala Pro Phe Thr Ser Trp Gly
                85                  90                  95

Asn Arg Leu Gln Val Arg Met Ser Gly Glu Glu Gln Lys Lys Arg Ile
            100                 105                 110

Leu Ala Ala Lys Lys Glu Arg Phe Pro Gly Trp Asp Gly Gly Leu His
        115                 120                 125

Gly Arg Gly Asp Gln Arg Ala Asp Ala Leu Phe Tyr Ala Val Thr Gln
    130                 135                 140

Pro Phe Pro Gly Ser Gly Glu Glu Gly His Gly Leu Phe Gln Pro Tyr
145                 150                 155                 160

Pro Asp Gln Pro Gly Lys Phe Tyr Ala Arg Trp Gly Leu Tyr Gly Pro
                165                 170                 175

```
Pro His Asp Ser Ala Pro Pro Asp Gly Ser Val Pro Lys Trp Glu Gly
            180                 185                 190

Thr Pro Glu Asp Asn Phe Leu Met Leu Arg Ala Ala Lys Tyr Phe
        195                 200                 205

Gly Ala Gly Gly Val Gly Ala Leu Asn Leu Ala Asp Pro Lys Cys Lys
            210                 215                 220

Lys Leu Ile Tyr Lys Lys Ala Gln Pro Met Thr Leu Gly Lys Gly Thr
225                 230                 235                 240

Tyr Ser Glu Ile Gly Gly Pro Gly Met Ile Asp Ala Lys Ile Tyr Pro
            245                 250                 255

Lys Val Pro Asp His Ala Val Pro Ile Asn Phe Lys Glu Ala Asp Tyr
            260                 265                 270

Ser Tyr Tyr Asn Asp Ala Glu Trp Val Ile Pro Thr Lys Cys Glu Ser
            275                 280                 285

Ile Phe Thr Phe Thr Leu Pro Gln Pro Gln Glu Leu Asn Lys Arg Thr
290                 295                 300

Gly Gly Ile Ala Gly Ala Gly Ser Tyr Thr Val Tyr Lys Asp Phe Ala
305                 310                 315                 320

Arg Val Gly Thr Leu Val Gln Met Phe Ile Lys Tyr Leu Gly Tyr His
            325                 330                 335

Ala Leu Tyr Trp Pro Ile Gly Trp Gly Pro Gly Gly Cys Phe Thr Thr
            340                 345                 350

Phe Asp Gly Gln Gly Glu Gln Gly Arg Thr Gly Ala Ala Ile His Trp
            355                 360                 365

Lys Phe Gly Ser Ser Gln Arg Gly Ser Glu Arg Val Ile Thr Asp Leu
370                 375                 380

Pro Ile Ala Pro Thr Pro Pro Ile Asp Ala Gly Met Phe Glu Phe Cys
385                 390                 395                 400

Lys Thr Cys Tyr Ile Cys Arg Asp Val Cys Val Ser Gly Gly Val His
            405                 410                 415

Gln Glu Asp Glu Pro Thr Trp Asp Ser Gly Asn Trp Asn Val Gln
            420                 425                 430

Gly Tyr Leu Gly Tyr Arg Thr Asp Trp Ser Gly Cys His Asn Gln Cys
            435                 440                 445

Gly Met Cys Gln Ser Ser Cys Pro Phe Thr Tyr Leu Gly Leu Glu Asn
            450                 455                 460

Ala Ser Leu Val His Lys Ile Val Lys Gly Val Val Ala Asn Thr Thr
465                 470                 475                 480

Val Phe Asn Ser Phe Phe Thr Asn Met Glu Lys Ala Leu Gly Tyr Gly
            485                 490                 495

Asp Leu Thr Met Glu Asn Ser Asn Trp Trp Lys Glu Glu Gly Pro Ile
            500                 505                 510

Tyr Gly Phe Asp Pro Gly Thr
            515
```

BACTERIUM THAT CAN PERFORM COMPLETE DECHLORINATION OF TRICHLOROETHENE AND THE METHOD TO DECHLORINATE SOILS OR GROUND WATER CONTAMINATED WITH TRICHLOROETHENE USING THE BACTERIUM

TECHNICAL FIELD

This invention relates to the bacterium that can be applied for bioremediation, and the method for dechlorination of soils or groundwater contaminated with trichloroethene.

BACKGROUND ART

Among the volatile chlorinated hydrocarbons, the chloroethenes (common name: chloroethylenes) such as tetrachloroethene (PCE) and trichloroethene (TCE), are major environmental contaminants which cause soils and ground water contamination. There are biological, chemical and physical means to treat soil and ground water contaminated chloroethenes. In the biological methods, microbial activities are used to degrade the contaminants. Chemical oxidants are used to degrade contaminants in chemical method. In physical approach, contaminated soils or ground water is removed or replaced. Among them, a biological method, in situ bioremediation, using anaerobic processes by supplying hydrogen-releasing compounds is thought to be the most promising means of cleaning up soils or groundwater contaminated with chloroethenes.

The biological method utilizes dehalorespiration performed in some microbes including *Dehalococcoides* species that uses chlorinated organic compounds as electron acceptors under anaerobic conditions. In this method, PCE and TCE are reductively dechlorinated via the less chlorinated ethenes, cis-1,2-dichloroethene (cis-DCE) and vinyl chloride (VC) to harmless ethene.

*Dehalococcoides* and *Desulfitobacterium* species are known as the microbes that are used for bioremediation of soils or ground water contaminated by chloroethenes. The previous studies on them are summarized as follows. Non-patent document 1 is the report on isolation of *Dehalococcoides ethenogenes* 195 that performs complete dechlorination of PCE to ethene. Non-patent document 2 describes that *Dehalococcoides* sp. BAV1 was isolated as the first anaerobic bacterium that dechlorinates VC and DCE to ethene. Non-patent documents 3 and 4 describe isolation of *Dehalococcoides* sp. VS that dechlorinates cis-1,2 DCE and VC to ethene and isolation of *Dehalococcoides* sp. FL2 that dechlorinates TCE and DCE to VC, respectively. In non-patent document 5, isolation and characterization of *Dehalococcoides* sp. GT that dechlorinates TCE through cis-1.2 DCE and VC to ethene are described.

As *Desulfitobacterium* strains, *Desulfitobacterium dehalogenance*, was reported in non-patent document 6. Patent document 1 and 2 refer to *Desulfitobacterium* strains that dechlorinate PCE, such as *Desulfitobacterium* sp. Y51 and *Desulfitobacterium* sp. KBC1.

According to reductive dehalogenases that are responsible for dechlorination of chloroethene, there are following documents: Patent documents 3 and 4 refer to PCE reductive dehalogenase (PCE). Non-patent document 7 refers to TCE reductive dehalogenase (TceA), and non-patent documents 8 and 9 refer to two VC reductive dehalogenases (BvcA and VcrA).

Patent document 5 describes methods for identification and quantification of reductive dehalogenase genes in the sample obtained from the sites contaminated by chloroethenes. Preparation of microbes for bioaugmentation is described in patent document 6.

PRIOR ART DOCUMENTS

Patent Documents

Patent Document 1: Japanese Patent Application Laid-Open (kokai) No. 2001-269175
Patent Document 2: Japanese Patent Application Laid-Open (kokai) No. 2005-270970
Patent Document 3: Japanese Patent Application Laid-Open (kokai) No. 2010-119339
Patent Document 4: Japanese Patent Application Laid-Open (kokai) No. 2006-042815
Patent Document 5: Japanese Patent Application Laid-Open (kokai) No. 2007-089560
Patent Document 6: Japanese Patent Application Laid-Open (kokai) No. 2007-104916

Non-Patent Documents

Non-Patent Document 1: Appl Environ Microbiol. 1999 July; 65(7):3108-13, Reductive dechlorination of chlorinated ethenes and 1,2-dichloroethane by "*Dehalococcoides ethenogenes*" 195, Maymo-Gatell X, Anguish T, Zinder S H.
Non-Patent Document 2: He J, Ritalahti K M, Yang K L, Koenigsberg S S, Löffler F E., Nature. 2003 Jul. 3; 424 (6944):62-5, Detoxification of vinyl chloride to ethene coupled to growth of an anaerobic bacterium.
Non-Patent Document 3: Cupples A M, Spormann A M, McCarty P L., Appl Environ Microbiol. 2003 February; 69(2):953-9, Growth of a *Dehalococcoides*-like microorganism on vinyl chloride and cis-dichloroethene as electron acceptors as determined by competitive PCR.
Non-Patent Document 4: He J, Sung Y, Krajmalnik-Brown R, Ritalahti K M, Löffler F E., Environ Microbiol. 2005 September; 7(9):1442-50, Isolation and characterization of *Dehalococcoides* sp. strain FL2, a trichloroethene (TCE)- and 1,2-dichloroethene-respiring anaerobe.
Non-Patent Document 5: Sung Y, Ritalahti K M, Apkarian R P, Löffler F E., Appl Environ Microbiol. 2006 March; 72(3):1980-7, Quantitative PCR confirms purity of strain GT, a novel trichloroethene-to-ethene-respiring *Dehalococcoides* isolate.
Non-Patent Document 6: Utkin I, Woese C, Wiegel J., Isolation and characterization of *Desulfitobacterium dehalogenans* gen. nov., sp. nov., an anaerobic bacterium which reductively dechlorinates chlorophenolic compounds, Int J Syst Bacteriol. 1994
Non-Patent Document 7: Magnuson J K, Romine M F, Burris D R, Kingsley M T., Appl Environ Microbiol. 2000 December; 66(12):5141-7, Trichloroethene reductive dehalogenase from *Dehalococcoides ethenogenes*: sequence of tceA and substrate range characterization.
Non-Patent Document 8: Krajmalnik-Brown R, Holscher T, Thomson I N, Saunders F M, Ritalahti K M, Löffler F E., Genetic identification of a putative vinyl chloride reductase in *Dehalococcoides* sp. strain BAV1, Appl Environ Microbiol. 2004 October; 70(10):6347-51.
Non-Patent Document 9: Appl Environ Microbiol. 2004 August; 70(8):4880-8, Muller J A, Rosner B M, Von Abendroth G, Meshulam-Simon G, McCarty P L, Spormann A M. Molecular identification of the catabolic vinyl chloride reductase from *Dehalococcoides* sp. strain VS and its environmental distribution.

SUMMARY OF THE INVENTION

Technical Problem

Reductive dechlorination of PCE and TCE (upstream dechlorination) are performed by several bacteria species including *Dehalococcoides* sp. strains. On the contrary, only limited members of *Dehalococcoides* sp. strains (*Dehalococcoides* sp., BAV1, VS, etc.) can dechlorinate DCE and VC to ethene (downstream dechlorination).

Thus, even if electron donors such as HRC (Hydrogen Releasing Compound) composed of poly-lactic acids are administrated into the grounds contaminated with chloroethenes, dechlorination will not proceed in the absence of such microbes. So the administration may be not effective in all soils contaminated by chloroethenes. In the absence of the *Dehalococcoides* sp. strains responsible for the downstream dechlorination, DCE or VC that are more toxic than PCE of TCE might accumulate in the grounds.

To avoid such problems, bioaugmentation, administration of cultivated microbes that can dechlorination such as *Dehalococcoides* strains, into the contaminated grounds have been proposed. However, it is very difficult to isolate and culture *Dehalococcoides* sp. strains. Thus, only a limited number of strains are available for such purpose. Moreover, it is necessary to administrate two different microbes that can perform upstream and downstream dechlorination. It is especially difficult to culture microbes responsible for downstream dechlorination. It is also very difficult to culture different strains in the grounds concertedly. Among *Dehalococcoides* strains, only *Dehalococcoides ethenogenes* 195 can dechlorinate PCE to ethene. However, *Dehalococcoides ethenogenes* 195 does not contain VC reductive dehalogenase gene. Thus, as VC is slowly degraded by co-metabolic pathway, toxic VC might accumulate. *Dehalococcoides* sp. GT has VC reductive dehalogenase gene (vcrA) and can dechlorinate TCE to ethene. However, due to the lack of TCEase gene, TCE degradation seems to be slow.

Objects of the present invention are to provide a novel *Dehalococcoides* sp. strain that can dechlorinate TCE to ethene, and bacteria consortium that contains the *Dehalococcoides* sp. strain, and in addition, to provide a method for dechlorination of soils or ground water contaminated by TCE by using the strain or consortium.

Solution to Problem

In order to attain the above objects, we have firstly constructed several bacteria consortia that can dechlorinate cis-1,2 DCE to ethene from ground water taken from several sites. Among them, one consortium was revealed to be able to dechlorinate TCE to ethene.

Sequence of the 16S rRNA gene has shown that the consortium is mainly composed of *Dehalococcoides* strain. Further analysis of reductive dehalogenase genes, the strain was found to be a novel strain that contains not only the TCEase gene, tceA, but also two VCase genes, bvcA and vcrA.

Accordingly, this invention provides *Dehalococcoides* sp. strain that has trichloroethene reductive dehalogenase gene (tceA) and also two vinyl chloride reductive dehalogenase genes (bvcA and vcrA), and has capability to degrade trichloroethene to ethene (hereinafter the *Dehalococcoides* sp. strain may be referred to as "the microbe of the present invention), and bacteria consortium containing the microbe of the present invention (hereinafter the bacteria consortium may be referred to as "the bacteria consortium of the present invention).

This invention also provides a method for dechlorinating contaminant with chloroethenes, by using the microbe of the present invention or the bacteria consortium of the present invention (hereinafter the method may be referred to as "the method of the present invention).

Effects of the Invention

The present invention enables provision of *Dehalococcoides* sp. strain which is capable of dechlorinating chloroethenes such as trichloroethene, dichloroethene isomers, and vinyl chloride, to ethene, and bacteria consortium containing the *Dehalococcoides* sp. strain. In addition, the present invention enables provision of a method for dechlorination of contaminant such as soils contaminated with volatile pollutant or contaminated ground water by using the *Dehalococcoides* sp. strain or the bacteria consortium containing it.

BRIEF DESCRIPTION OF THE DRAWINGS

FIG. 6A shows the results of comparison of nucleotide sequences of 16S rRNA genes between *Dehalococcoides* sp. ATV1 (SEQ ID NO: 19) and *Dehalococcoides ethenogenes* (SEQ ID NO: 20).

FIG. 6B shows the result of comparison of the nucleotide sequences of tceA genes between *Dehalococcoides* sp. ATV1 and *Dehalococcoides ethenogenes* (SEQ ID NOs: 21 and 23, respectively). FIG. 6C shows the amino acid sequences deduced from the tceA genes of *Dehalococcoides* sp. ATV1 and *Dehalococcoides ethenogenes* (SEQ ID NOs: 22 and 24, respectively).

FIG. 6D shows the result of comparison of the nucleotide sequences of bvcA genes between *Dehalococcoides* sp. ATV1 and *Dehalococcoides* sp. BAV1 (SEQ ID NOs: 25 and 27, respectively). FIG. 6E shows the amino acid sequences deduced from the bvcA genes of *Dehalococcoides* sp. ATV1 and *Dehalococcoides* sp. BAV1 (SEQ ID NOs: 26 and 28, respectively).

FIG. 6F shows the result of comparison of the nucleotide sequences of vcrA genes between *Dehalococcoides* sp. ATV1 and *Dehalococcoides* sp. VS (SEQ ID NOs: 29 and 31, respectively). FIG. 6G shows the amino acid sequences deduced from the vcrA genes of *Dehalococcoides* sp. ATV1 and *Dehalococcoides* sp. VS (SEQ ID NOs: 30 and 32, respectively).

DETAILED DESCRIPTION OF THE INVENTION

The Microbe of the Present Invention

1) Summary

Figure 1:
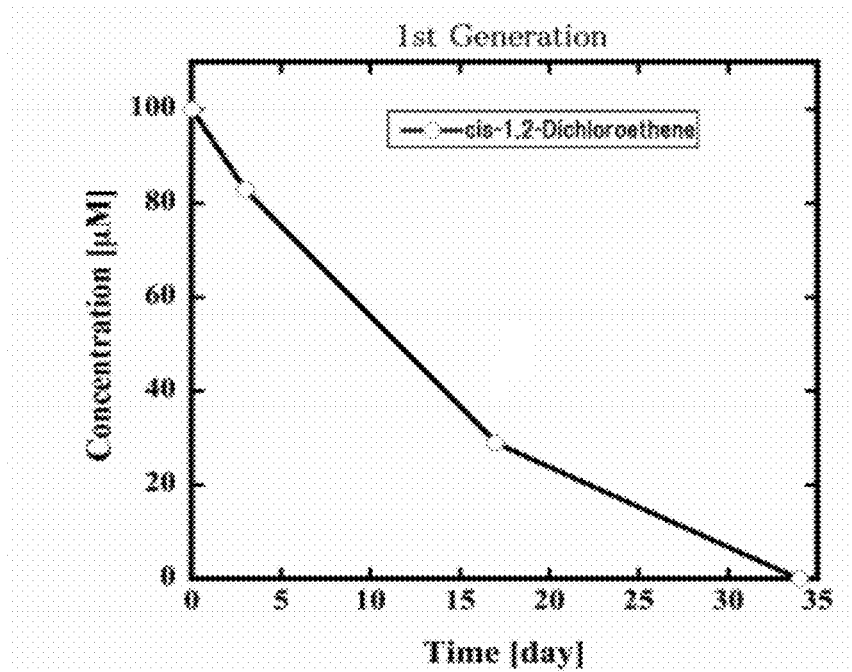
FIG. 1 shows the results of monitoring time course variation of cis-1,2 DCE concentration in case where ground water samples contaminated with TCE were cultured under anerobic conditions by using cis-1,2 DCE and hydrogen as substrates.

It might be possible to obtain the microbe that contains the TCE reductive dehalogenase gene, tceA, and VC reductive dehalogenase gene, bvcA or vcrA, by genetic manipulation. However, genetic manipulation for *Dehalococcoides* sp. strains or related microbes has not been established. Moreover, it will not be socially accepted to use genetically modified microbes for bioremediation. Therefore, it is expected to isolate microbes that can perform both upstream and downstream dechlorination of chloroethenes, from soils and ground water contaminated with chlorinated organic compound through a subculture method or enrich culture method. Thus, we have tried to culture imperceptible microbes that can dechlorinate cis-1,2 DCE and VC to ethene from the samples obtained from sites contaminated with chloroethenes, and have tried to isolate the microbe that can perform complete dechlorination of TCE to ethene. It is possible to analyze existence of TCEase gene, tceA, and VCase gene, bvcA or vcrA, by genetic analysis using PCR methods and sequencing. techniques. The outlines of processes of obtaining the microbe and the bacteria consortium of the present invention are as described below, which will be described in more detail in Examples.

2) Process of Obtaining the Microbe of the Present Invention

Groundwater was obtained from the ground contaminated with TCE and used as a source of bacterium. The primary cultures were carried out in the serum bottles containing sterilized mud, acetic acid, cis-DCE, and $H_2$ gas in the anaerobic condition. Several rounds of subcultures were performed by inoculation of about 4% culture after completion of dechlorination. Finally, the consortium that can dechlorinate 10 mg/L 1,2-cis DCE to ethene was established. That was confirmed by gas chromatography.

16S rRNA gene sequence has shown that *Dehalococcoides* sp. strains predominantly exist in the consortium. In addition, analysis of reductive dehalogenase genes has shown that the *Dehalococcoides* sp. strain is a novel one that contains two VC reductive dehalogenase genes, bvcA and vcrA, and in addition, tceA, that is TCEase gene. Therefore, the obtained consortium is a new consortium that contains the novel *Dehalococcoides* sp. strain. Genome analysis of the consortium by the next generation DNA sequencer, SOLiD 3, has shown the genome sequence *Dehalococcoides* strain is highly homologous to that of *Dehalococcoides ethenogenes* 195 and contains the TCEase gene, tceA. In addition, existence of two VCase genes, bvcA and vcrA, was also confirmed. As the coverage depths of tceA, Dehalococcoides 16S rRNA gene, bvcA and vcrA are similar and the consortium can dechlorinate TCE to ethene even after several rounds of culture in the medium containing 1,2-cis DCE, we concluded that the consortium contains the *Dehalococcoides* sp. strain contains tceA, bvcA and vcrA, and can dechlorinate TCE to ethene. The consortium containing the strain has been domestically deposited as *Dehalococcoides* sp. ATV1 at National Institute of Technology and Evaluation (NITE) Patent Microorganisms Depositary under Accession Number NITE BP-1018 (Deposit Date: Dec. 14, 2010).

The Method of the Present Invention

The method of the present invention is the method for dechlorination of contaminant with chloroethenes by administrating the strain or the consortium.

As used herein, the term "contaminant with chloroethenes" refers to contaminant which contains one or more chloroethenes selected from trichloroethene (TCE), dichloroethene isomers (DCE), and vinyl chloride (VC), and may contain other contaminants such as the first kind specified toxic substances, including tetrachloroethene (PCE), tetrachloromethane, 1,2 dichloroethane, 1,3 dichloropropene, dichloromethane, 1,1,1-trichloroethane, benzene, etc.; the second kind specified toxic substances, such as heavy metals, etc.; and the third kind specified toxic substances, such as agrichemicals etc., and may also contain oils and dioxins. Generally, contaminant is contaminated soils or ground water. Contaminated waste materials or mud may be included. Soils or ground water may be separated from the site (separated condition). Those in the contaminated site (unseparated condition) such as contaminated land side (including underground part), are also the targets of this invention.

In the separated condition, contaminated soils are removed from the site and dechlorination is performed outside (exo-situ bioremediation). The removed contaminated soils will be placed back to the site or other sites after dechlorination. This invention can be applied for various methods for exo-situ bioremediation including land farming, bio-piles, and slurry bioremediation. Land Farming is a bioremediation treatment process that is performed in the upper soil zone or in biotreatment cells. Contaminated soils, sediments, or sludges are incorporated into the soil surface and periodically turned over (tilled) to aerate the mixture. Bio-pile is a bioremediation technology in which excavated soils are mixed with soil amendments, formed into compost piles, and enclosed for treatment. Bio-slurry is the controlled treatment of excavated soil in an enclosed vessel.

As nutrition for bioremediation, electron donors, such as Hydrogen Releasing Compounds (HRC) (Regenesis), ADEKA geomate (ADEKA), EDC (Ecocycle) should be included. It is also possible to use hydrogen gas or acetic acid.

Treatment in the unseparated condition means the treatment in situ, in situ bioremediation. Since the invented microbes are absolute anaerobic, it is better to use them for in situ bioremediation. It is better to administrate the microbes and electron donors, such as HRC, from one or more wells located upstream of the contaminated site for in situ bioremediation. The microbes and electron donors will flow gradually by groundwater and dechlorination of chloroethenes to ethene over the whole area will be performed.

The microbes developed in this invention are absolute anaerobes, and thus it is difficult to perform high-density culture. Although it is possible to administer the culture microbes directly to the well(s) in the contaminated ground, it is necessary to concentrate the microbes and perform administration in anaerobic condition for more efficient bioremediation. One of the possible various methods is immobilization of the microbe. It is possible to use sodium alginate or κ-carrageenan that are generally used for immobilization of microbes. It is also possible to encapsulate the microbes in micro-capsules. Controlled release of microbes can be performed using biodegradable plastics such as polylactic acid etc., or temperature sensitive polymers such as poly(N-isopropyl acrylamido) etc. Immobilized microbes can be prepared by mixing the microbes with supporting materials. In case that the immobilized microbes are shaped as small beads, it is possible to administer as slurry into the well by pressurization. As this method also reduced exposure volume of microbes to air, it is the appropriate method for administrating anaerobic microbes.

To perform in situ bioremediation, treatability test is generally performed to examine the existence and dechlorination ability beforehand. This invention will enable to perform dechlorination of the grounds that was diagnosed to be difficult to clean up by treatability test. As treatability test requires several months, it is very useful to be able to skip the test process by perform the method of this invention. This invention will reduce the cost and time required for in situ bioremediation. Compared with the prior art for bioremediation of soils or groundwater contaminated with chloroethenes, the method proposed by this invention is highly advantageous in easiness, cost and effectiveness.

Growth of microbes is monitored by identification and quantification of genes including 16S rRNA gene amplification by real time PCR. It is also possible to monitor growth of microbes by various methods such as Denaturing Gradient Gel Electrophoresis, Fluorescence in situ hybridization, Quinone profile method, Direct viable counting, and viable cell counting methods using 6-carboxyfluorescein diacetate or 5-cyano-2,3-ditolyl tetrazolium chloride.

EXAMPLES

The present invention will next be described in detail by way of examples, which should not be construed as limiting the invention thereto.

By the following procedures, *Dehalococcoides* sp. ATV1 was obtained from the ground water contaminated by TCE and characterization was performed.

1. Preparation of Mineral Base Medium

A 1 L medium bottle containing 900 mL of deionized water was autoclaved and the following solutions and reagents were added.

| | |
|---|---|
| 10 mL | 100 × Salt stock solution |
| 1 mL | Trace element solution A |
| 1 mL | Trace element solution B |
| 50 μL | Resazurin sodium salt solution (0.5% w/v) |
| 1 mM | Potassium acetate |
| 0.206 g | L-Cysteine |
| 2.52 g | Sodium carbonate |
| 0.048 g | Sodium sulfide•2H$_2$O |

Autoclaved deionized water was added up to 1 L, and pH was adjusted to 7.0-7.5 with CO$_2$ gas.

100× Salt stock solution, Trace element solution A and Trace element solution B were prepared as follows.
(1) 100× Salt stock solution: 100 g NaCl, 50 g MgCl$_2$.6H$_2$O, 20 g KH$_2$PO$_4$, 30 g NH$_4$Cl, 30 g KCl, 1.5 g CaCl$_2$.2H$_2$O/1 L
(2) Trace element solution A: 10 mL HCl (25% solution, w/w), 1.5 g FeCl$_2$.4H$_2$O, 0.19 g CoCl$_2$.6H$_2$O, 0.1 g MnCl$_2$.4H$_2$O, 70 mg ZnCl$_2$, 6 mg H$_3$BO$_3$, 36 mg Na$_2$M$_O$O$_4$.2H$_2$O, 24 mg NiCl$_2$.6H$_2$O, 2 mg CuCl$_2$.2H$_2$O/1 L
(3) Trace element solution B: 6 mg Na$_2$SeO$_3$.5H$_2$O, 8 mg Na$_2$WO$_4$.2H$_2$O, 0.5 g NaOH/1 L 2. Sampling Ground water obtained from 9 m depth at Atsuta City, Aichi prefecture in Japan was used as the source of microbes. The ground water was contaminated with TCE, and by administration of hydrogen releasing compounds, *Dehalococcoides* sp. was increased and dechlorination of TCE to ethene was enhanced. The ground water was taken in anaerobic manner and kept at 4° C. during transportation. The sample was applied for culture immediately after the arrival.

3. Quantification of Chloroethenes and Ethene

Chloroethenes and ethene in the head-space were quantified by gas chromatography (GC-2014, Shimadzu) with FID (flame ionization detector) using the capillary column, DB-64 (60 m×0.32 mm, 1.80 μm width, J & W Co.). Sampling was performed using a gas tight syringe (Hamilton). The condition is as follows: Pressure at the inlet: 206.6 kPa; Column flow rate: 4.93 ml/min; Linear rate: 49.3 cm/s; Split ratio: 25.0; Total flow rate: 131.2 ml/min; Injection mode: SPLITLESS; Control mode: liner rate; Carrier gas: He. The temperatures at the inlet and the detector are 200° C. and 250° C., respectively. Oven temperature was kept at 35° C. for 15 mins, increased up to 75° C. with 4° C./min, and then increased up to 200° C. with 40° C./min. Retention times for TCE, cis-1,2 DCE, VC and ethene were 10.5, 7.5, 2.8 and 2.1 mins, respectively.

4. Culture of the First Generation.

10 g of autoclaved mud and 40 mL of mineral base medium was added in a vial bottle (100 mL, 40.5 mm outer diameter× 128 mm height). After sterilization by autoclave, at room-temperature liquid and gas phase replacement was performed using argon gas for about 5 min until the red color of resazurin in the medium disappeared. Then 50 mL of the sample ground water was added to the vial bottle. After sealing with a Teflon® coated butyl septum (GLscience Co. Ltd.) and aluminum seal (GLscience Co. Ltd.), argon gas replacement with injection needles (22 G×70, 18 G×1½, Terumo Co. Ltd.) was conducted for further 5 mins. 1 mL of hydrogen gas (3.3% of head-space volume) was added to each vial bottle using 5 ml syringes (NIPRO syringe GA). Finally, cis-1,2 DCE was added to be about 10 ppm using syringes with injection needles (Terumo25×1). All vial bottles were kept upside down at 25° C. in the dark condition. Gentle shaking was performed once in every three days. FIG. 1 shows a graph for the decrease of cis-1.2 DCE in a vial bottle. After 34 days culture, almost all cis-1.2 DCE was consumed.

5. Culture of Second Generation

Subculture was performed 37 days after the start of culture as almost all cis-1,2 DCE has disappeared. 10 g of autoclaved mud and 86.4 mL of mineral base medium was added in a 100 mL vial bottle. After sterilization by autoclave, 3.6 ml of the first generation culture was added. After sealing with a Teflon® coated butyl septum and aluminum seal, argon gas replacement was conducted for about 5 mins. 1 mL of hydrogen gas (3.3% of head-space volume) was added to each vial bottle using 5 ml syringe. Finally, cis-1,2 DCE was added to be about 10 ppm. All vial bottles were kept upside down at 25° C. in the dark condition. Gentle shaking was performed once in every three days.

6. Subcultures

Figure 2:
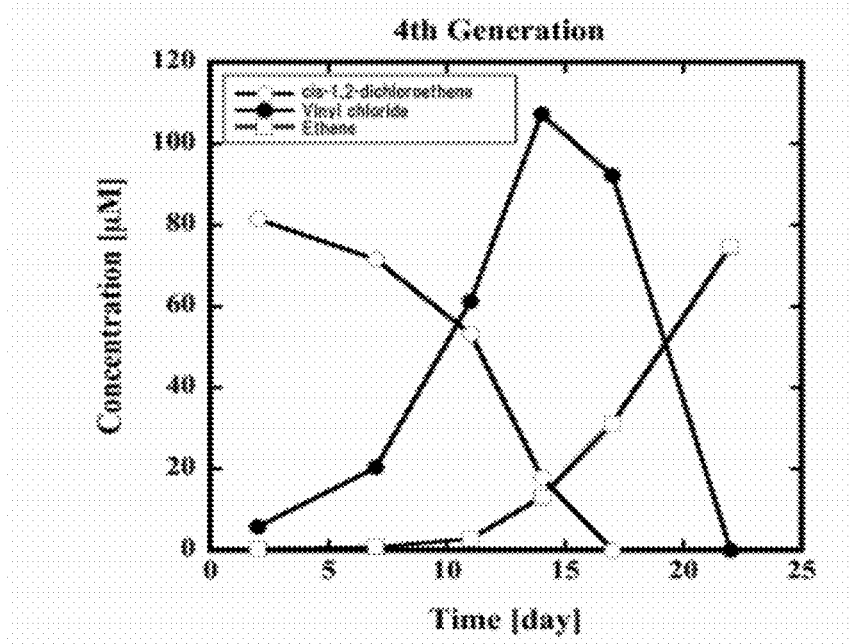
FIG. 2 shows the changes of cis-1,2 DCE, VC and TCE in the medium of the 4th generation.

Subcultures after third generations were done using 600 ml bottles (NICHIDEN-RIKA GLASS Co. Ltd.) with the following conditions.
  Subculture volumes: 4% of final volume
  Volume of medium: 75% of the bottle volume
  Amount of hydrogen: 5% of head space volume
  Amount of sterile mud: 5 weight % of fmal volume FIG. 2 shows the change of cis-1,2 DCE, VC and TCE in the medium of the 4$^{th}$ generation. As the decrease of cis-1,2 DCE, VC appeared, and then almost all cis-1,2 DCE was converted to ethene in three weeks. Almost same degradation rate was observed in the following generations.

7. Extraction of Genomic DNA

Total genomic DNA of bacteria in the sampled ground water and the 4$^{th}$ generation of the consortium was extracted by PowerMax™ Soil DNA Isolation Kit (MO-BIO). 90 ml of ground water or the culture media of consortia was centrifuged for 60 min at 20,000×g. The precipitants were resuspended in 15 ml of Bead Solution in Bead Solution Tubes. After vortex for 1 min, 1.2 mL of Solution S1 was added and vortexed for 30 sec. After adding 4 mL of Solution IRS, incubation was performed putting the tube in water bath heated at 65° C. with shaking with the maximum speed with vortex every 10 min. After centrifugation at 2,500×g for 3 mins, the supernatant was carefully taken and put in a new collection tube (50 mL). 2 mL of Solution S2 was added to the tube. After gentle shaking, the tube was placed on ice for 10 mins.

Supernatant was carefully taken after centrifugation at 2,500×g for 4 mins and put into a new collection tube (50 mL). 30 mL of Solution S3 was added to the tube and transferred to a Spin filters unit in 50 mL after gentle shaking. Filtration was performed by centrifugation at 2,500×g for 2 mins, and the filtrated liquid was discarded. Them the filter was washed using 6 mL of Solution S4 with centrifugation at 2,500×g for 3 mins. The Spin filter was placed in a new collection tube. 30 mL of Solution S5 was put on the Spin filter, and the genome DNA was extracted by centrifugation at 2,500×g for 3 mins.

8. Detection of *Dehalococcoides* sp. by Real-Time PCR.

Using Real-Time PCR, quantification of *Dehalococcoides* sp. strain responsible for dechlorination of cis-1,2 DCE in the ground water and the culture solution was performed. The targets of analysis are *Dehalococcoides* 16S rRNA genes, VC reductive dehalogenase of *Dehalococcoides* sp. BAV1, bvcA, and VC reductive dehalogenase of *Dehalococcoides* sp. VS, vcrA. Sequences of primes and probes used are shown in Table 1. Real-Time PCR was performed by StepOne™ Real-Time PCR System (Applied Biosystems). Standard curves were made using samples containing $10^3$-$10^7$ copies of genes in 1 μL.

Real-Time PCR of 16S rRNA gene and bvcA was performed using the mixture of 0.3 mM Forward Primer, 0.3 mM Reverse Primer, 0.3 mM Probe, 2× TaqMan®, Universal PCR Master Mix (Applied Biosystems), 3 μL Sample DNA and Distilled Water DNAse RNAse Free (Invitrogen) up to 30 μL. The Real-Time PCR mixture for vcrA is 0.3 mM Forward Primer, 0.3 mM Reverse Primer, 1× Fast SYBR® Green Master Mix (Applied Biosystems), 2 μL Sample DNA and Distilled Water DNAse RNAse Free up to 20 μL.

TABLE 1

Primers and probes for Real Time PCR

| Target | Primer/Probe | Sequence | Tm (° C.) |
|---|---|---|---|
| *Dehalococcoides* 16S rRNA gene | RTmDhcF | 5'-CTGGAGCTAATCCCCAAAGCT-3' (SEQ ID NO: 1) | 65.4 |
| | RTmDhcR | 5'-CAACTTCATGCAGGCGGG-3' (SEQ ID NO: 2) | 67.9 |
| | Probe | 5'-FAM-CCTCAGTTCGGATGC-MGB-3' (SEQ ID NO: 3) | |
| BvcA | VCR925F | 5'-AAAAGCACTTGGCTATCAAGGAC-3' (SEQ ID NO: 4) | 64.3 |
| | VCR1017R | 5'-CCAAAAGCACCACCAGGTC-3' (SEQ ID NO: 5) | 65.5 |
| | Probe | 5'-FAM-CTATGGCGACCGCAGG-MGB-3' (SEQ ID NO: 6) | |
| VcrA | vcrA_qPCR_Fw | 5'-CTCGGCTACCGAACGGATT-3' (SEQ ID NO: 7) | 58.2 |
| | vcrA_qPCR_Rv | 5'-GGGCAGGAGGATTGACACAT-3' (SEQ ID NO: 8) | 58.3 |

The sequence numbers 1 to 8 were allocated to the sequences of primes and probes in descending order in Table 1.

9. Occupancy of *Dehalococcoides* sp. in the Bacteria Consortium

Table 2 shows the amount of genome DNA and also the copy numbers of *Dehalococcoides* 16S rRNA genes. The results show that *Dehalococcoides* sp. was about 1% in the beginning and increased up to 90% in the consortium of 4th generation.

TABLE 2

| Sample | Total DNA (ng) | *Dehalococcoides* 16S rRNA gene (copies/sample) | Estimated *Dehalococcoides* Genome DNA (ng) | Occupancy of *Dehalococcoides* |
|---|---|---|---|---|
| Ground water (100 ml) | $2.0 \times 10^3$ | $1.5 \times 10^7$ | $2.5 \times 10$ | 1.3% |
| 4$^{th}$ Generation (600 ml) | $1.5 \times 10^4$ | $8.3 \times 10^9$ | $1.4 \times 10^4$ | 93.3% |

10. Quantification of Reductive Dehalogenase Genes

Figure 3:
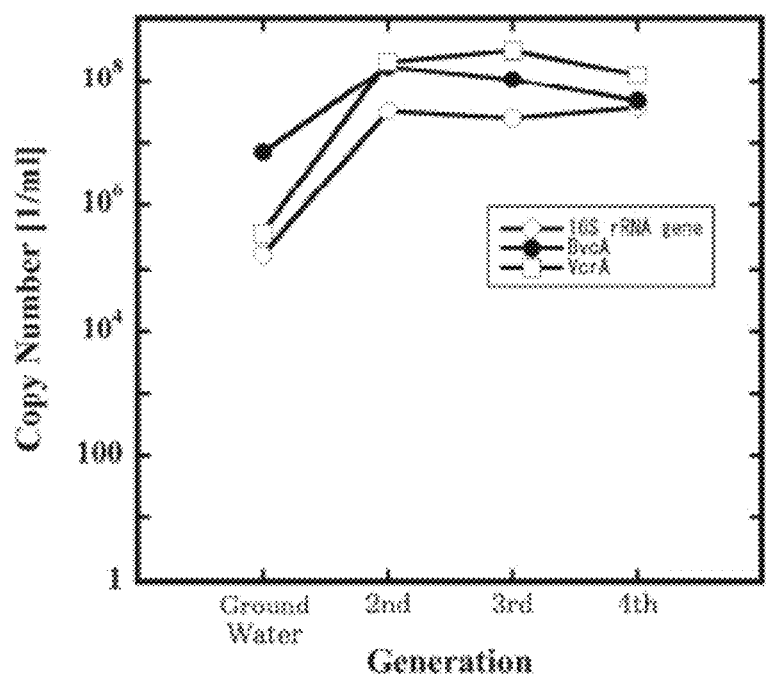
FIG. 3 shows the results of quantification of *Dehalococcoides* 16S rRNA gene and VC reductive dehalogenase genes (bvcA and vcrA) by real time PCR in every generation.
Figure 4A:
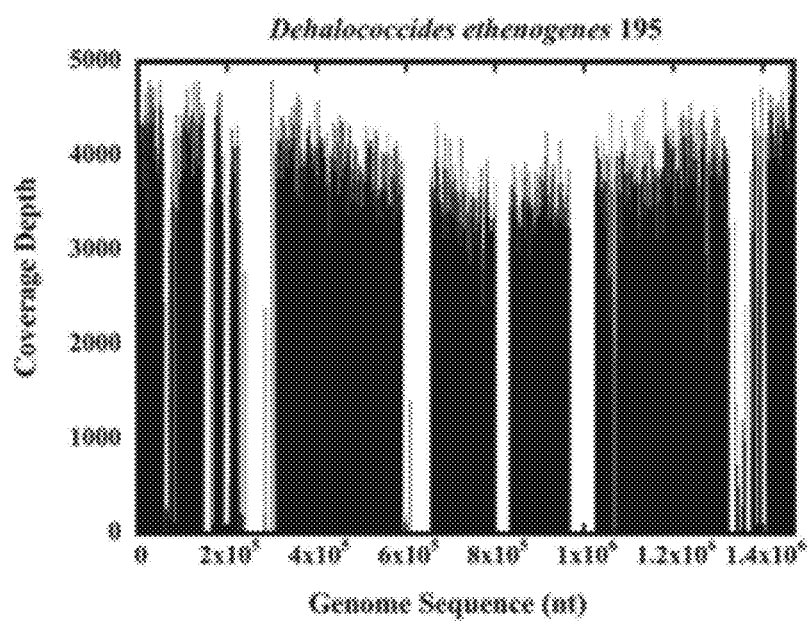
FIGS. 4A-4E show the results of genome matching between genome sequences of (1) *Dehalococcoides ethenogenes* 195, (2) *Dehalococcoides* sp. BAV1, (3) *Dehalococcoides* sp. CBDB1, (4) *Dehalococcoides* sp. VS, and (5) *Dehalococcoides* sp. GT, using the next generation DNA sequencer, SOLiD 3 (Life Technologies).
Figure 4B:
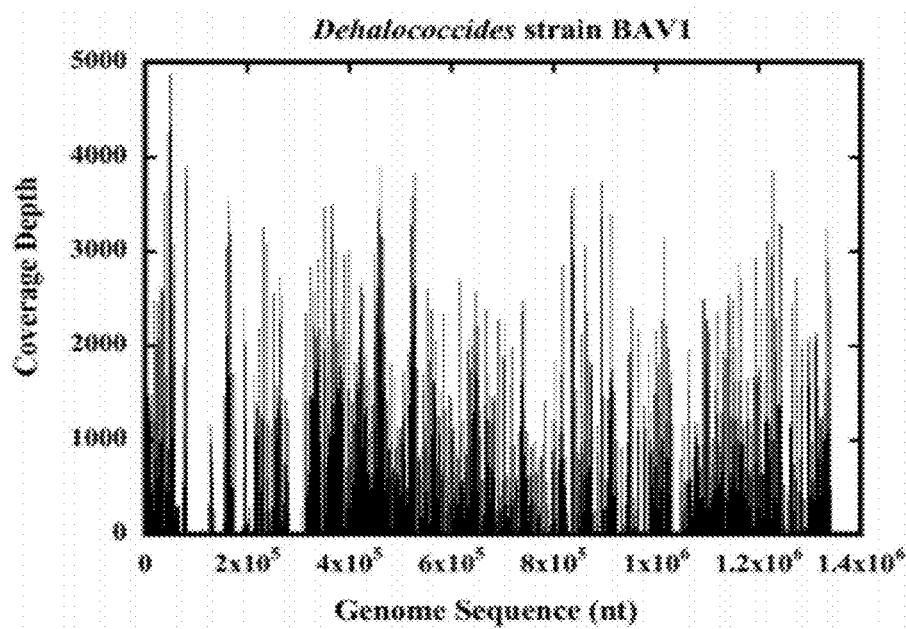
Figure 4C:
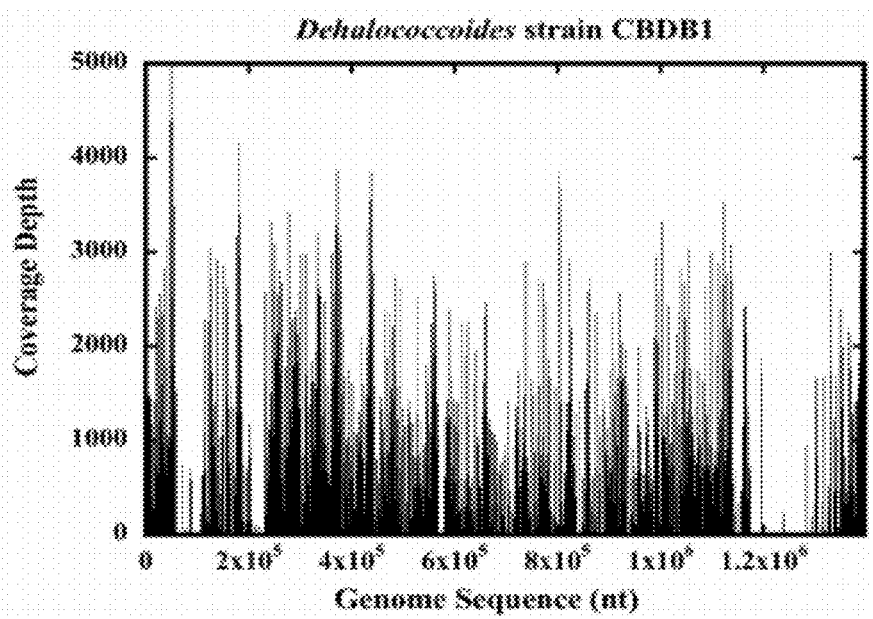
Figure 4D:
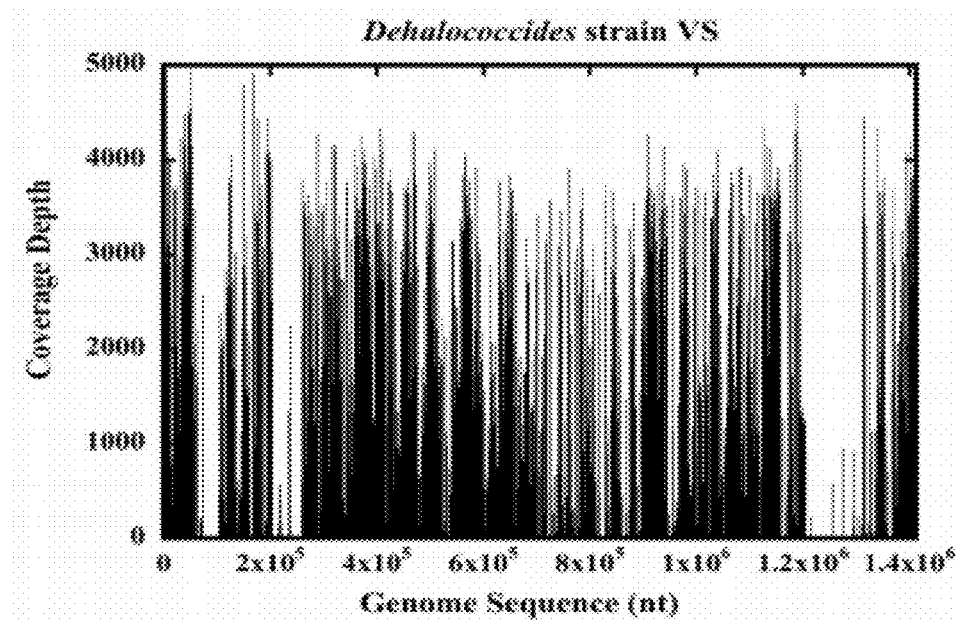
Figure 4E:
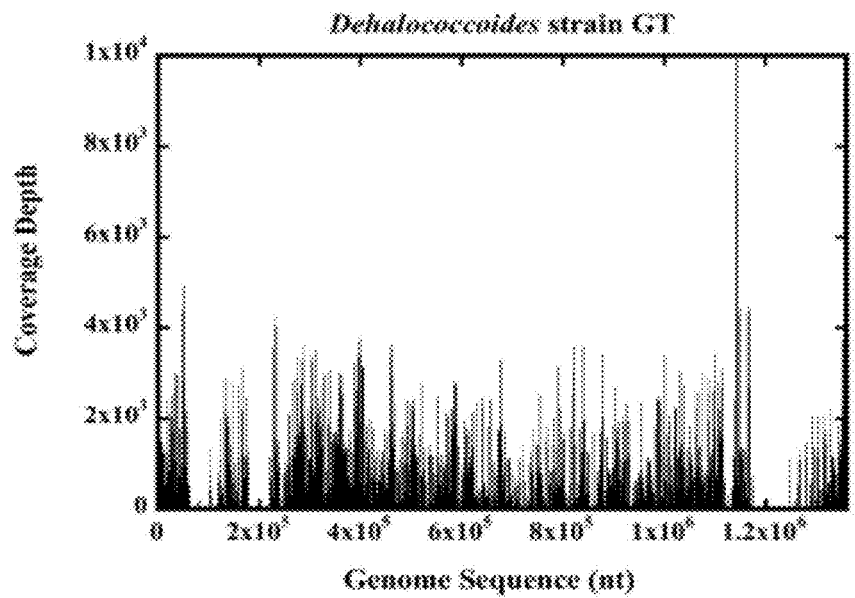

Genes for 16S rRNA and reductive dehalogenases, vcrA and bvcA, were quantified for each generation by real time PCR (FIG. 3). In spite of some differences of increasing efficiency, the number of vcrA and bvcA genes varied with the number of 16S rRNA gene for each generation. The variation patterns are similar to each other. It is suggested that one *Dehalococcoides* sp. strain contains both genes.

11. Analysis of the Bacteria in the Consortium by Genome Analysis—Comparison with other Genome Sequences of *Dehalococcoides* sp. Strains As *Dehalococcoides* sp. strains dominantly exist in the 4th generation of the bacteria consortium, genome analysis of the consortium was performed using the next generation DNA sequencer SOLiD 3 (Life Technologies). Total genomic DNA was purified from the consortium and treated as recommended. The obtained data were applied for comparison with genome sequences of (1) NC_002936 (*Dehalococcoides ethenogenes* 195), (2) NC_009455 (*Dehalococcoides* sp. BAV1), (3) NC_007356 (*Dehalococcoides* sp. CBDB1), (4) NC_013552 (*Dehalococcoides* sp. VS), (5) NC_013890 (*Dehalococcoides* sp. GT) using the software, Corona Lite. The results are shown in FIGS. 4A-4E. In SOLiD 3 genome sequences are obtained as tag sequences of 50 bases. Comparing the tag sequences with reference genome sequence, the numbers of tag sequences matched with allowance of 3 mismatches (Coverage Depth) are shown. The result clearly shows that the *Dehalococcoides* sp. strain in the consortium is highly homologous to *Dehalococcoides ethenogenes* 195 in genome sequence.

12. Analysis of Reductive Dehalogenase Genes

To examine existence of reductive dehalogenase genes, coverage depths for reductive dehalogenase genes were analyzed. Tables 3, 4, 5 and 6 show the average values of coverage depths for reductive dehalogenase genes found in the genomes of *Dehalococcoides* sp. strains.

Among 17 reductive dehalogenase genes in *Dehalococcoides ethenogenes* 195, existence of 7 genes including TCE reductive dehalogenase, tceA, was confirmed. Although almost no reductive dehalogenase genes of other *Dehalococcoides* sp. strains exhibited significant coverage values, existence of VC reductive dehalogenase genes, bvcA of *Dehalococcoides* sp. Bav1 and vcrA of *Dehalococcoides* sp. VS, were observed. This result is consistence of the results of real time PCR for these genes.

The results of real time PCR have demonstrated that the *Dehalococcoides* sp. strain to have bvcA and vcrA is dominant in the consortium. As the coverage depths of them are similar to those of 7 reductive dehalogenase genes of *Dehalococcoides ethenogenes* 195 including tceA, it is suggested that the *Dehalococcoides* sp. strain highly homologous to *Dehalococcoides ethenogenes* 195 contains tceA, bvcA and vcrA. On the contrary, the PCE reductive dehalogenase gene, pceA, does not exit in the genome of the *Dehalococcoides* sp. strain.

TABLE 3

Coverage values of reductive dehalogenase genes of *Dehalococcoides ethenogenes* 195

| Gene | Strand | Start | Stop | Coverage |
|---|---|---|---|---|
| DET0079(TceA) | − | 77229 | 78893 | 2042 |
| DET0173 | + | 167859 | 169391 | 836 |
| DET0180 | + | 173382 | 174749 | 3718 |
| DET0235 | + | 226290 | 227762 | 54 |
| DET0302 | + | 290049 | 291593 | 1 |

TABLE 3-continued

Coverage values of reductive dehalogenase genes of *Dehalococcoides ethenogenes* 195

| Gene | Strand | Start | Stop | Coverage |
|---|---|---|---|---|
| DET0306 | + | 294215 | 295732 | 0 |
| DET0311 | + | 298706 | 300253 | 0 |
| DET0318(PceA) | + | 304666 | 306153 | 0 |
| DET0876 | − | 803653 | 805185 | 0 |
| DET1171 | − | 1067812 | 1069410 | 0 |
| DET1519 | − | 1371471 | 1372988 | 0 |
| DET1522 | − | 1374234 | 1375757 | 905 |
| DET1528 | − | 1379479 | 1380888 | 3373 |
| DET1535 | − | 1384117 | 1385601 | 2500 |
| DET1538 | − | 1386684 | 1388162 | 8 |
| DET1545 | − | 1392249 | 1393751 | 409 |
| DET1559 | − | 1404340 | 1405788 | 0 |

TABLE 4

Coverage values of reductive dehalogenase genes of *Dehalococcoides* sp. BAV1

| Gene | Strand | Start | Stop | Coverage |
|---|---|---|---|---|
| DehaBAV1_0104 | − | 103582 | 105129 | 0 |
| DehaBAV1_0112 | − | 111779 | 113299 | 0 |
| DehaBAV1_0119 | − | 117096 | 118538 | 0 |
| DehaBAV1_0121 | − | 119160 | 120704 | 0 |
| DehaBAV1_0173 | − | 173374 | 174741 | 279 |
| DehaBAV1_0276 | + | 288132 | 289703 | 0 |
| DehaBAV1_0281 | − | 293045 | 294457 | 0 |
| DehaBAV1_0284 | − | 295198 | 296688 | 0 |
| DehaBAV1_0296 | + | 305957 | 307495 | 0 |
| DehaBAV1_0847(BvcA) | − | 834960 | 836510 | 2432 |

TABLE 5

Coverage values of reductive dehalogenase genes of *Dehalococcoides* sp. CBDB1

| Gene | Strand | Start | Stop | Coverage |
|---|---|---|---|---|
| cbdb_A80 | + | 61449 | 62939 | 0 |
| cbdb_A84 | + | 67523 | 68989 | 0 |
| cbdb_A88 | − | 72513 | 74060 | 0 |
| cbdb_A96 | − | 80710 | 82230 | 0 |
| cbdb_A187 | + | 170338 | 171705 | 225 |
| cbdb_A238 | + | 208160 | 209704 | 0 |
| cbdb_A243 | + | 213820 | 215295 | 7 |
| cbdb_A1092 | + | 885869 | 887467 | 0 |
| cbdb_A1453 | − | 1146028 | 1147515 | 0 |
| cbdb_A1455 | − | 1148252 | 1149745 | 0 |
| cbdb_A1491 | − | 1177174 | 1178622 | 0 |
| cbdb_A1495 | − | 1183152 | 1184669 | 0 |
| cbdb_A1503 | − | 1189522 | 1191102 | 0 |
| cbdb_A1508 | − | 1193343 | 1194734 | 0 |
| cbdb_A1535 | + | 1222599 | 1224086 | 0 |
| cbdb_A1539 | − | 1226459 | 1227841 | 0 |
| cbdb_A1542 | − | 1228967 | 1230430 | 0 |
| cbdb_A1546 | − | 1233683 | 1235200 | 0 |
| cbdb_A1550 | − | 1237886 | 1239412 | 47 |
| cbdb_A1560 | − | 1245976 | 1247517 | 0 |
| cbdb_A1563 | − | 1248605 | 1250002 | 0 |
| cbdb_A1570 | − | 1257652 | 1259175 | 0 |
| cbdb_A1575 | − | 1263534 | 1265051 | 0 |
| cbdb_A1578 | − | 1266472 | 1267989 | 0 |
| cbdb_A1582 | + | 1269916 | 1271391 | 0 |
| cbdb_A1588 | − | 1274257 | 1275744 | 0 |
| cbdb_A1595 | − | 1283001 | 1284485 | 74 |
| cbdb_A1598 | − | 1285951 | 1287450 | 0 |
| cbdb_A1618 | − | 1309684 | 1311111 | 2 |
| cbdb_A1624 | − | 1316903 | 1318390 | 0 |

TABLE 5-continued

Coverage values of reductive dehalogenase
genes of *Dehalococcoides* sp. CBDB1

| Gene | Strand | Start | Stop | Coverage |
|---|---|---|---|---|
| cbdb_A1627 | − | 1319491 | 1320969 | 4 |
| cbdb_A1638 | − | 1325086 | 1326588 | 47 |

TABLE 6

Coverage values of reductive dehalogenase genes
of *Dehalococcoides* sp. VS

| Gene | Strand | Start | Stop | Coverage |
|---|---|---|---|---|
| DhcVS_82 | − | 711113132 | 74556 | 0 |
| DhcVS_88 | − | 81035 | 82573 | 0 |
| DhcVS_96 | + | 90484 | 91974 | 0 |
| DhcVS_99" | + | 90484 | 91974 | 0 |
| DhcVS_104 | − | 97423 | 98994 | 0 |
| DhcVS_169 | + | 167053 | 168420 | 3162 |
| DhcVS_1260 | − | 1158576 | 1160105 | 0 |
| DhcVS_1263 | − | 1160729 | 1162222 | 0 |
| DhcVS_1291(VcrA) | − | 1187299 | 1188858 | 3271 |
| DhcVS_1314 | − | 1211229 | 1212674 | 0 |
| DhcVS_1316 | − | 1213448 | 1214932 | 21 |
| DhcVS_1320 | − | 1217638 | 1219167 | 0 |
| DhcVS_1324 | − | 1221945 | 1223426 | 0 |
| DhcVS_1327 | − | 1224558 | 1226057 | 0 |
| DhcVS_1329 | − | 1226677 | 1228098 | 0 |
| DhcVS_1336 | − | 1235559 | 1237049 | 0 |
| DhcVS_1340 | − | 1240073 | 1241515 | 0 |
| DhcVS_1342 | − | 1241951 | 1243372 | 0 |
| DhcVS_1344 | − | 1243835 | 1245301 | 0 |
| DhcVS_1347 | + | 1246808 | 1248097 | 0 |
| DhcVS_1349 | − | 1248692 | 1250077 | 0 |
| DhcVS_1353 | − | 1251497 | 1253041 | 0 |
| DhcVS_1360 | − | 1257634 | 1259232 | 0 |
| DhcVS_1364 | − | 1261258 | 1262814 | 0 |
| DhcVS_1371 | − | 1267664 | 1269181 | 0 |
| DhcVS_1375 | − | 1272030 | 1273547 | 0 |
| DhcVS_1378 | − | 1274677 | 1276203 | 171 |
| DhcVS_1383 | − | 1279450 | 1280967 | 0 |
| DhcVS_1387 | − | 1282905 | 1284380 | 0 |
| DhcVS_1393 | − | 1287013 | 1288500 | 0 |
| DhcVS_1399 | − | 1295467 | 1296951 | 131 |
| DhcVS_1402 | − | 1298295 | 1299794 | 0 |
| DhcVS_1421 | − | 1322374 | 1323801 | 16 |
| DhcVS_1427 | − | 1329484 | 1330974 | 0 |
| DhcVS_1430 | − | 1332053 | 1333531 | 4 |
| DhcVS_1436 | − | 1337642 | 1339213 | 29 |

13. Identification and Quantification of Microbes Constituting the Bacteria Consortium Comparison against almost all 16S rRNA genes in public database was performed in the similar manner. The result shows existence of 16S rRNA genes of microbes listed in Table 7. Comparing the coverage depths of them, the existence ratios of them were estimated. *Dehalococcoides* sp. strain was the most abundant species and was estimated to cover 47.1% of all microbes in the consortium. As the coverage depth of 16SrRNA gene was almost same as those of tceA, bvcA and vcrA, it is suggested that one *Dehalococcoides* sp. strain contains all tceA, bvcA and vcrA. If these genes are in different *Dehalococcoides* sp. strains, every number of them cannot be equal to 16S rRNA gene. Although there is a possibility that microbes that are not included in *Dehalococcoides* sp. strains have these reductive dehalogenase genes, it is very unplausible and also denied by the fact the coverage depths of them exceed those of 16S rRNA genes of other microbes. Therefore, we concluded that one *Dehalococcoides* sp. strain contains all tceA, bvcA and vcrA and named it as *Dehalococcoides* sp. ATV1.

This microbe has been deposited as a bacteria consortium at National Institute of Technology and Evaluation (NITE) Patent Microorganisms Depositary under Accession No. NITE BP-1018.

The existence ration estimated by this method is rather low compared with that estimated by real time PCR. It seems that the difference should be due to the over estimation by real time PCR.

TABLE 7

| Microbes whose existence was supported by comparison of 16S rRNA gene sequence | Coverage Depth | Existence ratio (%) |
|---|---|---|
| *Dehalococcoides* | 3141 | 47.1 |
| *Scarpharca* | 1556 | 23.4 |
| *Azospira* | 1026 | 15.4 |
| *Chlorobi* | 500 | 7.5 |
| *Actinobacter* | 439 | 6.6 |

To confirm the existence of these microbes in the bacteria consortium, PCR amplifications of the gene fragments specific for the microbes were performed on the total genome obtained from the consortium using the primers shown in Table 8.

TABLE 8

Sequences of PCR Primers for detection of microbes observed by genome analysis

| | Primers | Size of PCR Product |
|---|---|---|
| *Dehalococcoides* sp. | Fw 5'-CGCGGTAATACGTAGGAAGC -3' (SEQ ID NO: 9) <br> Rv 5'-CTCTGGTGTTCCTCCCGATA -3' (SEQ ID NO: 10) | 200 bp |
| *Chlorobi* sp. | Fw 5'-ATACGCGAGGAACCTTACCC -3' (SEQ ID NO: 11) <br> Rv 5'-GGCATCTTTACGATGGCAGT -3' (SEQ ID NO: 12) | 210 bp |
| *Actinobacterium* sp. | Fw 5'-ACAAGCGGTGGAGCATGTGG- 3' (SEQ ID NO: 13) <br> Rv 5'-GTAAGGTTCCTCGCGTACCA- 3' (SEQ ID NO: 14) | 80 bp |
| *Azospira* sp. | Fw 5'-TGGGGAGCAAACAGGATTAG -3' (SEQ ID NO: 15) | 200 bp |

TABLE 8-continued

Sequences of PCR Primers for detection of microbes observed by genome analysis

| | Primers | Size of PCR Product |
|---|---|---|
| | Rv 5'-CGTTGCATCGAATTAAACCA-3'<br>(SEQ ID NO: 16) | |
| Enterobacter sp. | Fw 5'-GAGCAAACAGGATTAGATAC-3'<br>(SEQ ID NO: 17)<br>Rv 5'-ACCCAACATCTCTACGACACG-3'<br>(SEQ ID NO: 18) | 318 bp |

The sequence numbers 9 to 18 were allocated to the sequences of primes and probes in descending order in Table 8.

Figure 5:
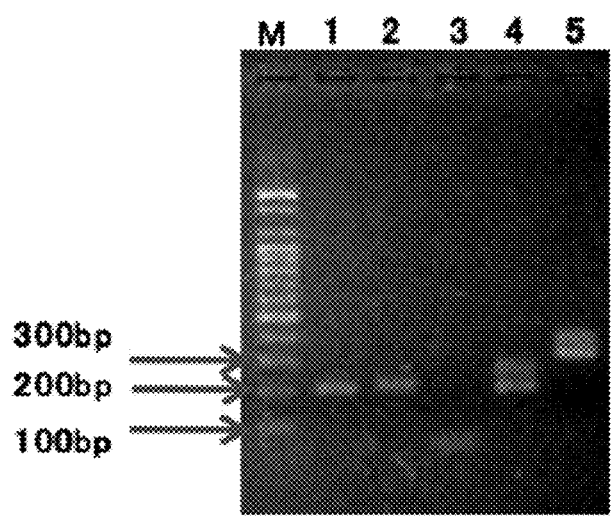
FIG. 5 shows the results of PCR amplification of 16S rRNA genes that are suggested to exist in the bacteria consortium.

The results of PCR are shown in FIG. 5. FIG. 5 shows the results of PCR amplification of specific gene fragments of microbes whose existence was suggested by genome analysis (M: Molecular Weight Marker (100 base ladder); 1: *Dehalococcoides* sp.; 2: *Chlobi* sp.; 3: *Actinobacterium* sp.; 4: *Azospira* sp.; 5: *Enterobacter* sp.). Existence of all strains was confirmed.

14. Cloning and Sequence of Genes for 16S rRNA and Reductive Dehalogenases

Figure 6A:
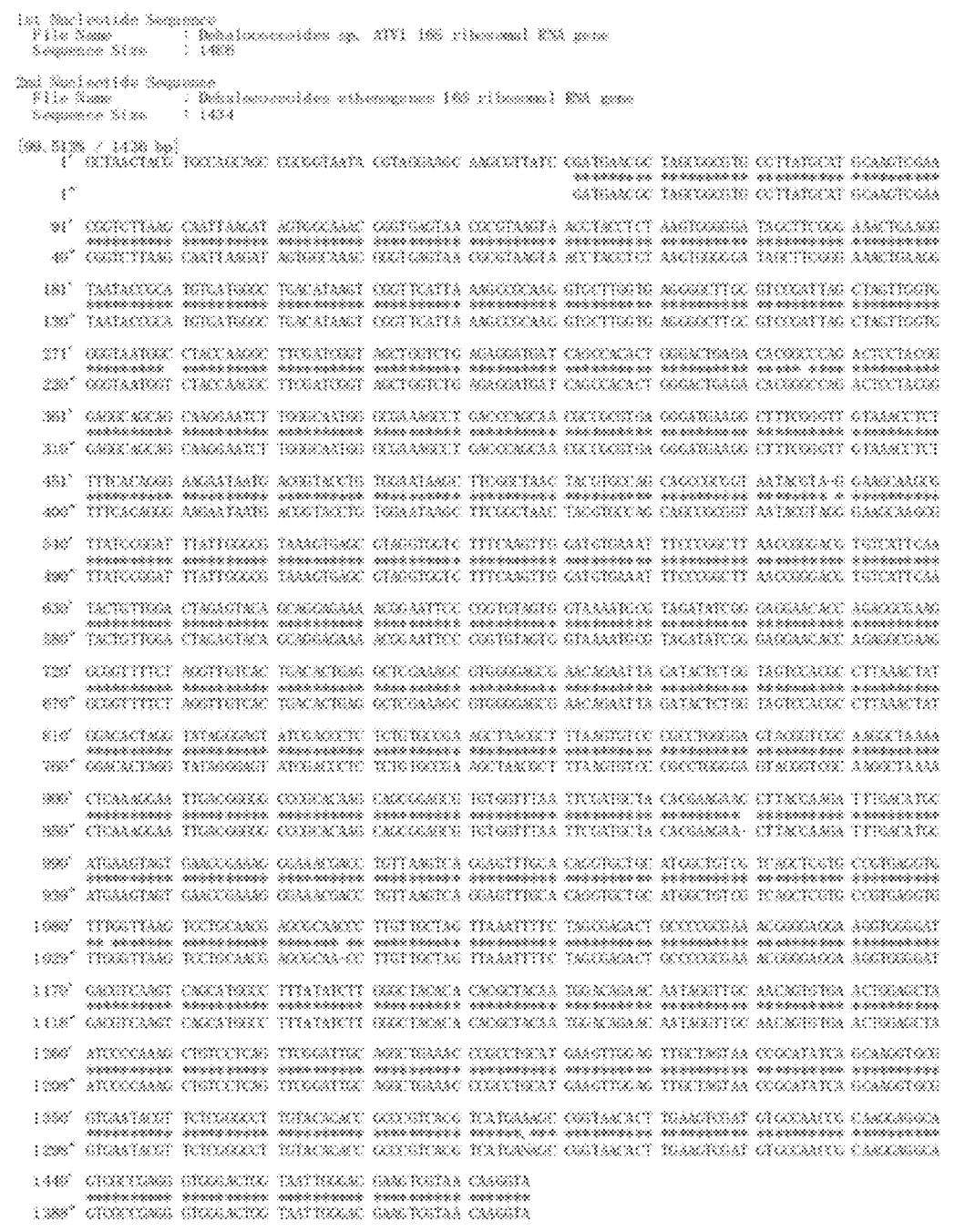

Genes for 16S rRNA and reductive dehalogenases, tceA, bvcA and vcrA, were amplified by PCR and nucleotide sequences of them were determined. Comparisons of them (DNA sequence, Amino acid sequence, their homology) with those of other *Dehalococcoides* sp. strains are shown in FIGS. 6A-6G. FIG. 6A shows the result of comparison of nucleotide sequences of 16S rRNA genes between *Dehalococcoides* sp. ATV1 and *Dehalococcoides ethenogenes* (sequence number 19: 16S rRNA gene sequence of *Dehalococcoides* sp. ATV1, sequence number 20: 16S rRNA gene sequence of *Dehalococcoides ethenogenes*).

Figure 6B:
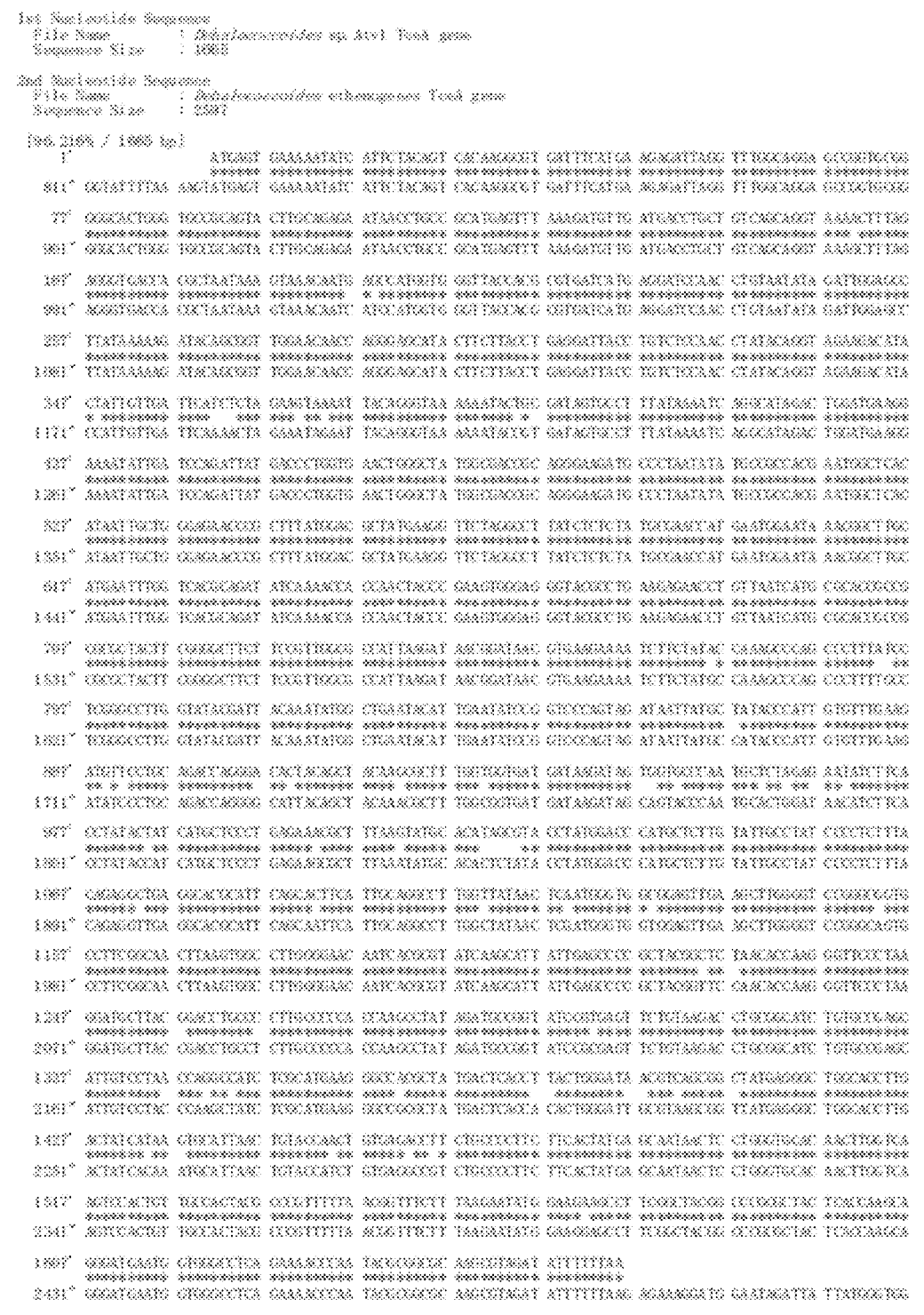
Figure 6C:
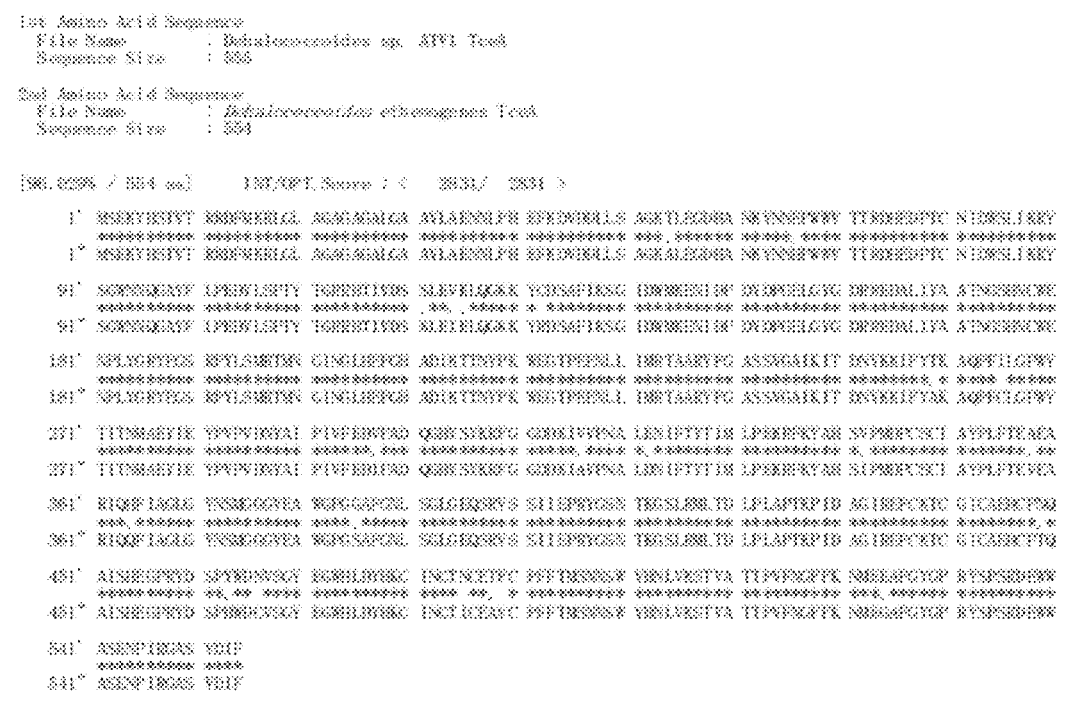

FIGS. 6B and 6C show the result of comparison of nucleotide sequences of tceA genes and amino acids between *Dehalococcoides* sp. ATV1 and *Dehalococcoides ethenogenes* (sequence number 21,22: tceA gene and amino acids sequence of *Dehalococcoides* sp. ATV1, sequence number 23,24: tceA gene and amino acids sequence of *Dehalococcoides ethenogenes*).

Figure 6D:
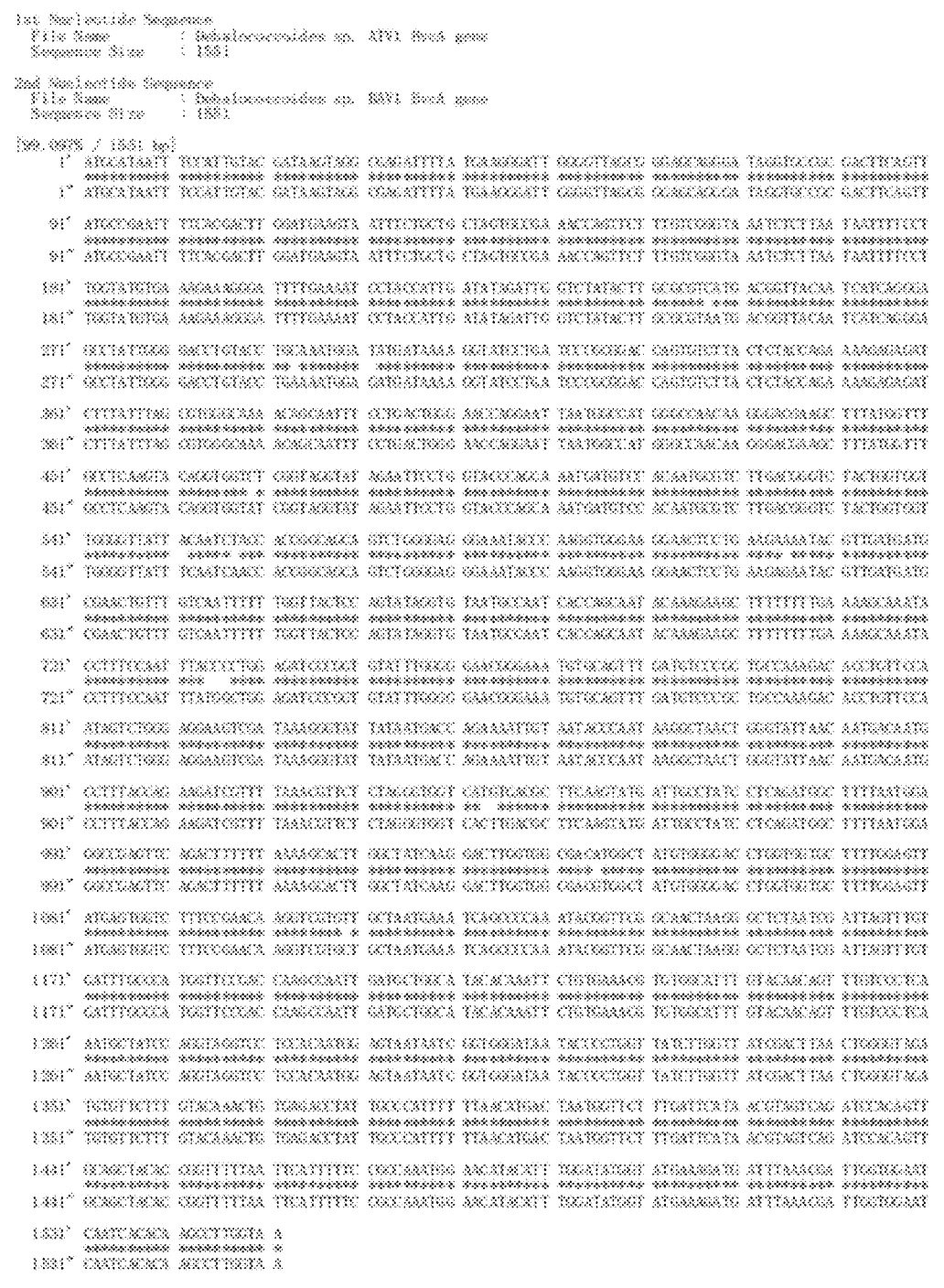
Figure 6E:
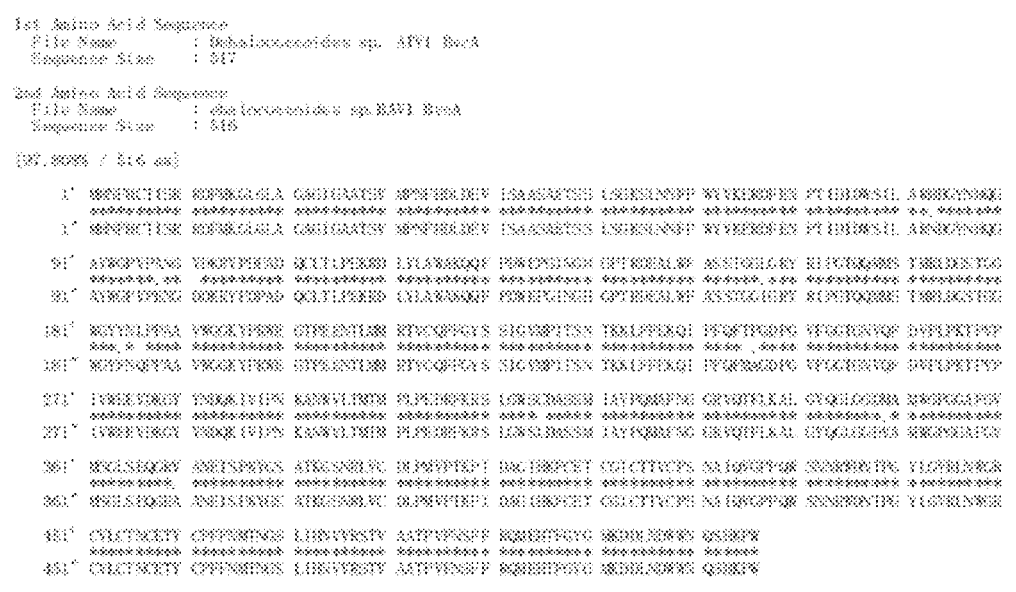

FIGS. 6D and 6E show the result of comparison of nucleotide sequences of bvcA genes and amino acids between *Dehalococcoides* sp. ATV1 and *Dehalococcoides ethenogenes* (sequence number 25,26: bvcA gene and amino acids sequence of *Dehalococcoides* sp. ATV1, sequence number 27,28: bvcA gene and amino acids sequence of *Dehalococcoides ethenogenes*).

Figure 6F:
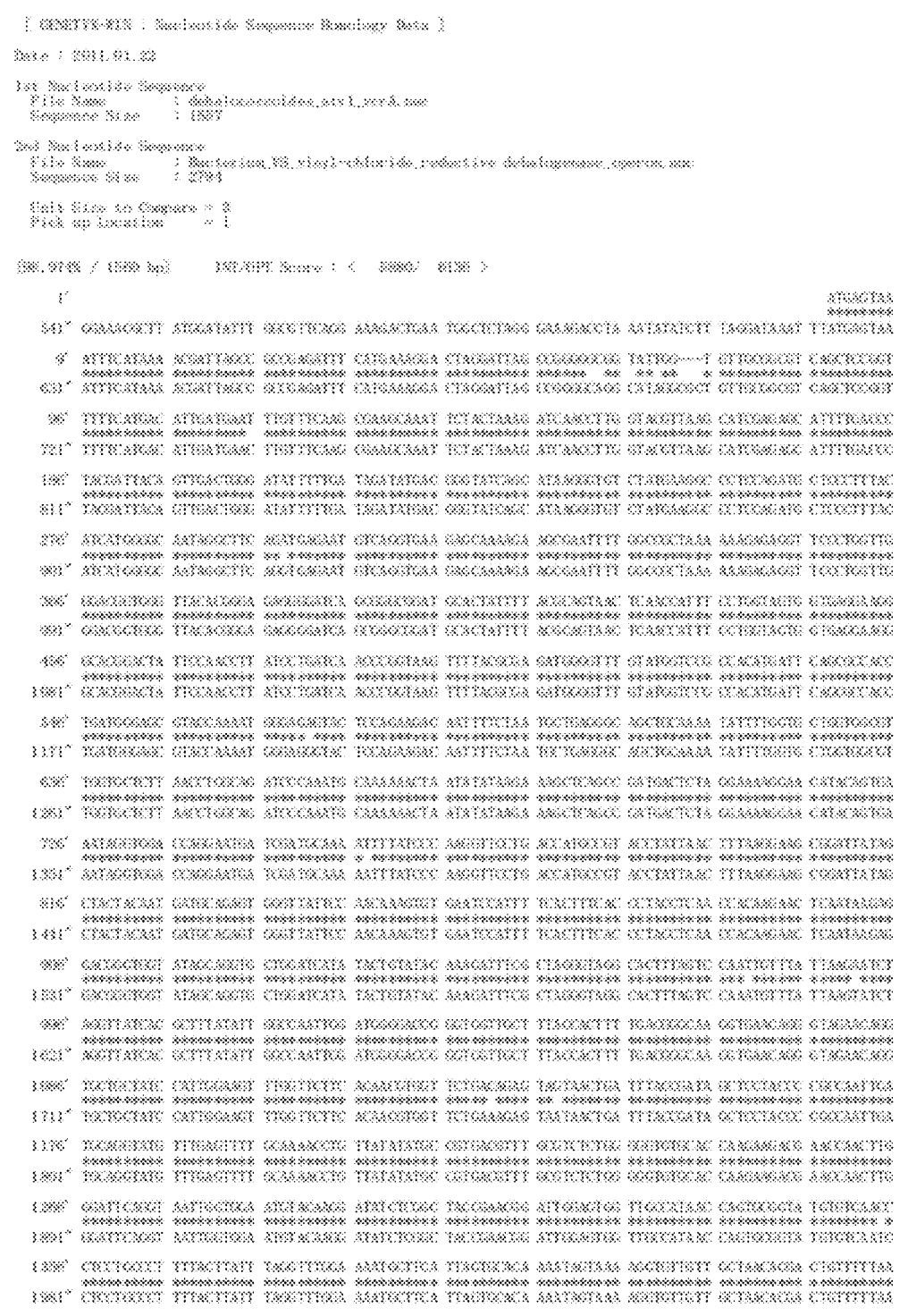
Figure 6G:
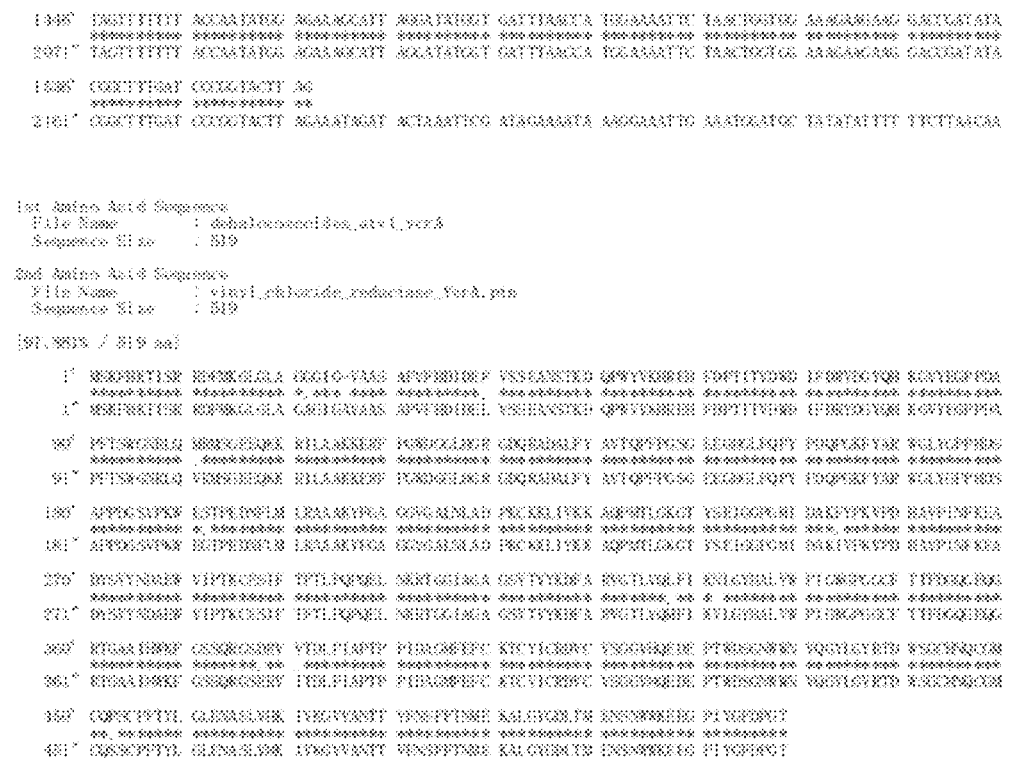

FIGS. 6F and 6G show the results of comparison of nucleotide sequences of vcrA genes and amino acids between *Dehalococcoides* sp. ATV1 and *Dehalococcoides ethenogenes* (sequence number 29,30: vcrA gene and amino acids sequence of *Dehalococcoides* sp. ATV1, sequence number 31,32: vcrA gene and amino acids sequence of *Dehalococcoides ethenogenes*).

15. Confirmation of Dechlorination Activity for TCE

Figure 7A:
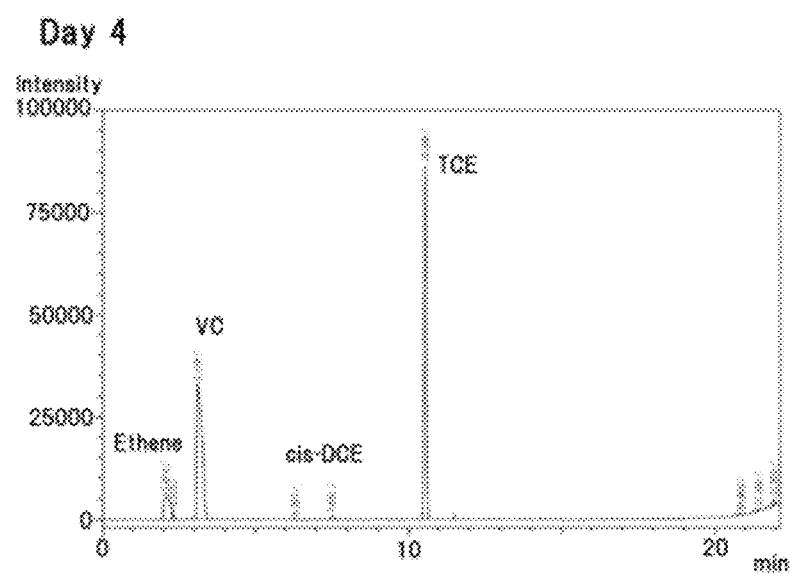
FIGS. 7A and 7B show the results of confirmation of TCE dechlorination activity
Figure 7B:
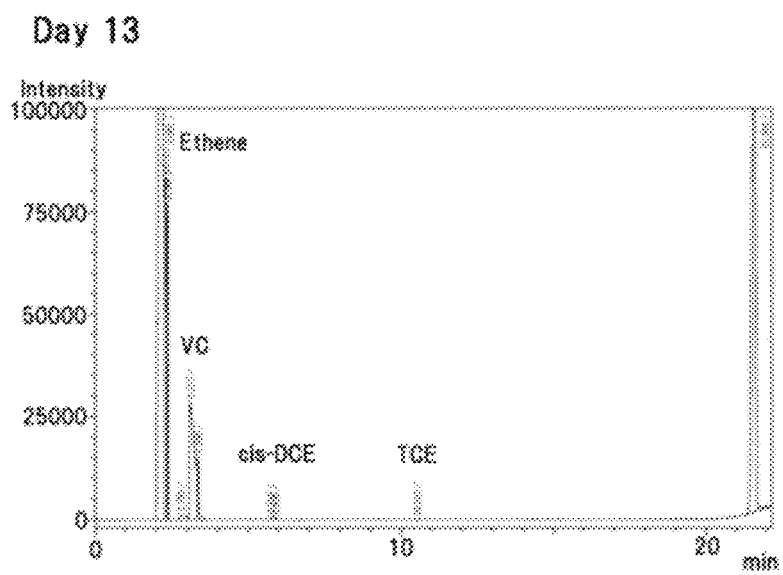

As the TCE reductive dehalogenase gene, tceA, was found in the genome of *Dehalococcoides* sp. ATV1 in the consortium, it is suggested that the strain can perform dechlorinate TCE to ethene. To confirm it, the cultivation of the consortium containing *Dehalococcoides* sp. ATV1 using TCE as electron acceptor was performed. Finally, 10 ppm of TCE was completely degraded by the consortium for about 13 days. Therefore, we concluded that *Dehalococcoides* sp. ATV1 could dechlorinate TCE to ethene. FIGS. 7A and 7B show the results of gas chromatography at 4 and 13 days after the culture. After 13 days, the peak for TCE has disappeared and the peak for ethene appeared.

16. Electron micrograph of *Dehalococcoides* sp. ATV1

Figure 8:
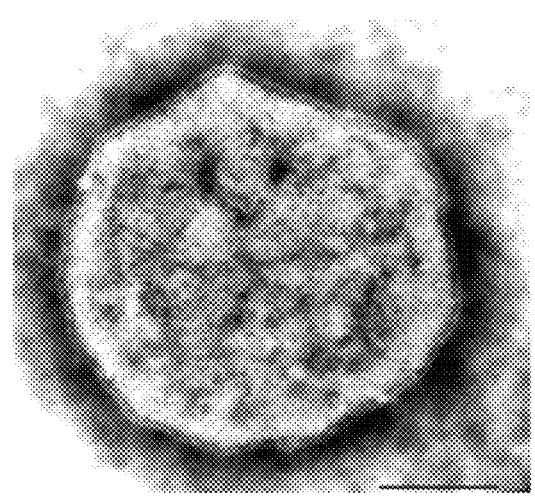
FIG. 8 shows the electron microscopic image of *Dehalococcoides* sp. strain obtained in this invention.

*Dehalococcoides* sp. ATV1 in the 4th culture was observed by electron microscopy (JEM-1400: maximum accelerating voltage:120 kV). The electron micrograph is shown in FIG. 8. The condition is as follows.

80 kV
    1% TPA staining
    200 mesh supporting grid 10000×

The observed shape was almost same as those of other *Dehalococcoides* sp. strains.

What is claimed is:

1. An isolated bacterial consortium which has been deposited under Accession No. NITE BP-1018.

2. A method for dechlorinating a contaminant with chloroethenes, said method comprising contacting the bacterial consortium of claim 1 with the contaminant with chloroethenes.

3. The method according to claim 2, wherein the contaminant is contaminated soil or ground water.

4. The method according to claim 2, wherein ethene is obtained as a final product.

* * * * *